US011317841B2

(12) United States Patent
Cadwell

(10) Patent No.: US 11,317,841 B2
(45) Date of Patent: May 3, 2022

(54) METHOD AND SYSTEM FOR ELECTRODE VERIFICATION

(71) Applicant: Cadwell Laboratories, Inc., Kennewick, WA (US)

(72) Inventor: John A. Cadwell, Richland, WA (US)

(*) Notice: Subject to any disclaimer, the term of this patent is extended or adjusted under 35 U.S.C. 154(b) by 349 days.

(21) Appl. No.: 16/683,528

(22) Filed: Nov. 14, 2019

(65) Prior Publication Data

US 2020/0146571 A1   May 14, 2020

Related U.S. Application Data

(60) Provisional application No. 62/767,504, filed on Nov. 14, 2018.

(51) Int. Cl.
*A61B 5/24* (2021.01)
*G06F 17/18* (2006.01)
(Continued)

(52) U.S. Cl.
CPC .............. *A61B 5/24* (2021.01); *A61B 5/291* (2021.01); *A61B 5/7221* (2013.01); *A61B 5/7225* (2013.01); *G06F 17/18* (2013.01)

(58) Field of Classification Search
CPC ......... G06F 17/18; A61B 5/7225; A61B 5/72; A61B 5/7214; A61B 5/721; A61B 5/7221;
(Continued)

(56) References Cited

U.S. PATENT DOCUMENTS

| 751,475 A | 2/1904 | De Vilbiss |
| 2,320,709 A | 6/1943 | Arnesen |

(Continued)

FOREIGN PATENT DOCUMENTS

| DE | 102014008684 A1 | 1/2016 |
| EP | 298268 | 1/1989 |

(Continued)

OTHER PUBLICATIONS

Aage R. Møller, "Intraoperative Neurophysiologic Monitoring", University of Pittsburgh, School of Medicine Pennsylvania, © 1995 by Harwood Academic Publishers GmbH.
(Continued)

*Primary Examiner* — Matthew Kremer
*Assistant Examiner* — Avery M Foley
(74) *Attorney, Agent, or Firm* — Novel IP

(57) ABSTRACT

An electrode management solution for neuromonitoring applications such as electroencephalography (EEG) procedures provides for the verification of the locations and connections of electrodes. The brain is modeled as a volume conductor and an expected attenuated signal generated by an electrical signal present in the form of an electrical dipole at any other point in the brain is calculated. A known signal is connected between electrodes at 'presumed' locations. This action generates a defined electrical field which can be measured between any of the other electrode locations. The amplitude and phase of the measured signals are a function of the input signal, the volume conductor, and the geometric relations of the two electrodes. By comparing the expected values with the measured values, the relation between the electrodes is verified.

20 Claims, 13 Drawing Sheets

(51) Int. Cl.
*A61B 5/00* (2006.01)
*A61B 5/291* (2021.01)

(58) Field of Classification Search
CPC .......... A61B 5/282; A61B 5/291; A61B 5/25; A61B 5/24; A61B 5/397; A61B 5/388; A61B 5/372; A61B 5/315; A61B 5/313; A61B 5/311; A61B 5/31; A61B 5/308; A61B 5/307; A61B 5/297; A61B 5/296; A61B 5/294; A61B 5/276; A61B 5/274; A61B 5/273; A61B 5/271; A61B 5/259; A61B 5/257; A61B 5/256; A61B 5/254; A61B 5/252; A61B 5/251; A61B 5/248; A61B 5/246; A61B 5/243; A61B 5/242; A61B 5/2415; A61B 5/26; A61N 1/0531
See application file for complete search history.

(56) References Cited

U.S. PATENT DOCUMENTS

| | | | |
|---|---|---|---|
| 2,807,259 | A | 9/1957 | Federico |
| 3,165,340 | A | 1/1965 | Kuehl |
| 3,659,250 | A | 4/1972 | Horton |
| 3,682,162 | A | 8/1972 | Colyer |
| 3,985,125 | A | 10/1976 | Rose |
| 3,993,859 | A | 11/1976 | McNeel |
| 4,155,353 | A | 5/1979 | Rea |
| 4,262,306 | A | 4/1981 | Renner |
| 4,263,899 | A | 4/1981 | Burgin |
| 4,545,374 | A | 10/1985 | Jacobson |
| 4,562,832 | A | 1/1986 | Wilder |
| 4,616,635 | A | 10/1986 | Caspar |
| 4,705,049 | A | 11/1987 | John |
| 4,716,901 | A | 1/1988 | Jackson |
| 4,743,959 | A | 5/1988 | Frederiksen |
| 4,765,311 | A | 8/1988 | Kulik |
| 4,817,587 | A | 4/1989 | Janese |
| 4,862,891 | A | 9/1989 | Smith |
| 4,889,502 | A | 12/1989 | Althouse |
| 4,914,508 | A | 4/1990 | Music |
| 5,107,845 | A | 4/1992 | Guern |
| 5,171,279 | A | 12/1992 | Mathews |
| 5,196,015 | A | 3/1993 | Neubardt |
| 5,284,153 | A | 2/1994 | Raymond |
| 5,284,154 | A | 2/1994 | Raymond |
| 5,299,563 | A | 4/1994 | Seton |
| 5,377,667 | A | 1/1995 | Patton |
| 5,438,989 | A | 8/1995 | Hochman |
| 5,462,448 | A | 10/1995 | Kida |
| 5,472,426 | A | 12/1995 | Bonati |
| 5,474,558 | A | 12/1995 | Neubardt |
| 5,540,235 | A | 7/1996 | Wilson |
| 5,544,286 | A | 8/1996 | Laney |
| 5,560,372 | A | 10/1996 | Cory |
| 5,565,779 | A | 10/1996 | Arakawa |
| 5,578,060 | A | 11/1996 | Pohl |
| 5,601,608 | A | 2/1997 | Mouchawar |
| 5,602,585 | A | 2/1997 | Dickinson |
| 5,625,759 | A | 4/1997 | Freeman |
| 5,648,815 | A | 7/1997 | Toba |
| 5,664,029 | A | 9/1997 | Callahan |
| 5,681,265 | A | 10/1997 | Maeda |
| 5,684,887 | A | 11/1997 | Lee |
| 5,728,046 | A | 3/1998 | Mayer |
| 5,741,261 | A | 4/1998 | Moskovitz |
| 5,772,661 | A | 6/1998 | Michelson |
| 5,775,331 | A | 7/1998 | Raymond |
| 5,775,931 | A | 7/1998 | Jones |
| 5,785,648 | A | 7/1998 | Min |
| 5,792,044 | A | 8/1998 | Foley |
| 5,795,291 | A | 8/1998 | Koros |
| 5,830,150 | A | 11/1998 | Palmer |
| 5,847,755 | A | 12/1998 | Wixson |
| 5,860,973 | A | 1/1999 | Michelson |
| 5,868,668 | A | 2/1999 | Weiss |
| 5,885,210 | A | 3/1999 | Cox |
| 5,891,147 | A | 4/1999 | Moskovitz |
| 5,928,139 | A | 7/1999 | Koros |
| 5,928,158 | A | 7/1999 | Aristides |
| 5,930,379 | A | 7/1999 | Rehg |
| 5,931,777 | A | 8/1999 | Sava |
| 5,933,929 | A | 8/1999 | Kawakami |
| 5,944,658 | A | 8/1999 | Koros |
| 5,954,635 | A | 9/1999 | Foley |
| 5,993,385 | A | 11/1999 | Johnston |
| 6,004,312 | A | 12/1999 | Finneran |
| 6,004,341 | A | 12/1999 | Zhu |
| 6,026,180 | A | 2/2000 | Wittenstein |
| 6,042,540 | A | 3/2000 | Johnston |
| 6,062,216 | A | 5/2000 | Corn |
| 6,074,343 | A | 6/2000 | Nathanson |
| 6,088,878 | A | 7/2000 | Antonucci |
| 6,095,987 | A | 8/2000 | Shmulewitz |
| 6,109,948 | A | 8/2000 | Kuo |
| 6,116,941 | A | 9/2000 | Kuo |
| 6,119,306 | A | 9/2000 | Antonucci |
| 6,139,493 | A | 10/2000 | Koros |
| 6,152,871 | A | 11/2000 | Foley |
| 6,181,961 | B1 | 1/2001 | Prass |
| 6,196,969 | B1 | 3/2001 | Bester |
| 6,206,826 | B1 | 3/2001 | Mathews |
| 6,210,202 | B1 | 4/2001 | Kuo |
| 6,224,545 | B1 | 5/2001 | Cocchia |
| 6,236,874 | B1 | 5/2001 | Devlin |
| 6,241,548 | B1 | 6/2001 | Kuo |
| 6,259,945 | B1 | 7/2001 | Epstein |
| 6,264,491 | B1 | 7/2001 | Lord |
| 6,266,558 | B1 | 7/2001 | Gozani |
| 6,273,740 | B1 | 8/2001 | Lord |
| 6,287,322 | B1 | 9/2001 | Zhu |
| 6,302,842 | B1 | 10/2001 | Auerbach |
| 6,306,100 | B1 | 10/2001 | Prass |
| 6,309,349 | B1 | 10/2001 | Bertolero |
| 6,325,764 | B1 | 12/2001 | Griffith |
| 6,334,068 | B1 | 12/2001 | Hacker |
| 6,373,890 | B1 | 4/2002 | Freeman |
| 6,425,859 | B1 | 7/2002 | Foley |
| 6,450,952 | B1 | 9/2002 | Rioux |
| 6,466,817 | B1 | 10/2002 | Kaula |
| 6,473,639 | B1 | 10/2002 | Fischell |
| 6,500,128 | B2 | 12/2002 | Marino |
| 6,535,759 | B1 | 3/2003 | Epstein |
| 6,579,114 | B2 | 6/2003 | Lord |
| 6,609,018 | B2 | 8/2003 | Cory |
| 6,712,795 | B1 | 3/2004 | Cohen |
| 6,799,931 | B2 | 10/2004 | Kwilosz |
| 6,805,668 | B1 | 10/2004 | Cadwell |
| 6,837,716 | B1 | 1/2005 | Brazas |
| 6,847,849 | B2 | 1/2005 | Mamo |
| 6,851,430 | B2 | 2/2005 | Tsou |
| 6,869,301 | B2 | 3/2005 | Shimizu |
| 6,870,109 | B1 | 3/2005 | Villarreal |
| 6,926,728 | B2 | 8/2005 | Zucherman |
| 6,945,933 | B2 | 9/2005 | Branch |
| 7,072,521 | B1 | 7/2006 | Cadwell |
| 7,089,059 | B1 | 8/2006 | Pless |
| 7,104,965 | B1 | 9/2006 | Jiang |
| 7,177,677 | B2 | 2/2007 | Kaula |
| 7,214,197 | B2 | 5/2007 | Prass |
| 7,230,688 | B1 | 6/2007 | Villarreal |
| 7,261,688 | B2 | 8/2007 | Smith |
| 7,374,448 | B1 | 5/2008 | Jepsen |
| 7,470,236 | B1 | 12/2008 | Kelleher |
| 7,522,953 | B2 | 4/2009 | Kaula |
| 7,713,210 | B2 | 5/2010 | Byrd |
| 7,801,601 | B2 | 9/2010 | Maschino |
| 7,914,350 | B1 | 3/2011 | Bozich |
| 7,963,927 | B2 | 6/2011 | Kelleher |
| 7,983,761 | B2 | 7/2011 | Giuntoli |
| 8,147,421 | B2 | 4/2012 | Farquhar |
| 8,160,694 | B2 | 4/2012 | Salmon |
| 8,192,437 | B2 | 6/2012 | Simonson |
| D670,656 | S | 11/2012 | Jepsen |

(56) References Cited

U.S. PATENT DOCUMENTS

| | | | |
|---|---|---|---|
| 8,323,208 B2 | 12/2012 | Davis | |
| 8,439,703 B2 | 5/2013 | Natoli | |
| 8,876,813 B2 | 11/2014 | Min | |
| 8,942,797 B2 | 1/2015 | Bartol | |
| 8,958,869 B2 | 2/2015 | Kelleher | |
| 9,084,551 B2 | 7/2015 | Brunnett | |
| 9,138,586 B2 | 9/2015 | Eiger | |
| 9,155,503 B2 | 10/2015 | Cadwell | |
| 9,295,401 B2 | 3/2016 | Cadwell | |
| 9,352,153 B2 | 5/2016 | Van Dijk | |
| 9,730,634 B2 | 8/2017 | Cadwell | |
| 10,238,467 B2 | 3/2019 | Cadwell | |
| 2002/0007188 A1 | 1/2002 | Arambula | |
| 2002/0009916 A1 | 1/2002 | Lord | |
| 2002/0088098 A1 | 7/2002 | Bouley | |
| 2002/0095080 A1 | 7/2002 | Cory | |
| 2003/0045808 A1 | 3/2003 | Kaula | |
| 2003/0074033 A1 | 4/2003 | Pless | |
| 2004/0030258 A1 | 2/2004 | Williams | |
| 2004/0127810 A1 | 7/2004 | Sackellares | |
| 2004/0192100 A1 | 9/2004 | Shimizu | |
| 2005/0003682 A1 | 1/2005 | Brazas | |
| 2005/0075578 A1 | 4/2005 | Gharib | |
| 2005/0085743 A1* | 4/2005 | Hacker | A61B 5/24 600/554 |
| 2005/0182454 A1 | 8/2005 | Gharib | |
| 2006/0009754 A1 | 1/2006 | Boese | |
| 2006/0085048 A1 | 4/2006 | Cory | |
| 2006/0085049 A1 | 4/2006 | Cory | |
| 2006/0122514 A1 | 6/2006 | Byrd | |
| 2006/0135877 A1 | 6/2006 | Giftakis | |
| 2006/0258951 A1 | 11/2006 | Bleich | |
| 2007/0016097 A1 | 1/2007 | Farquhar | |
| 2007/0021682 A1 | 1/2007 | Gharib | |
| 2007/0032841 A1 | 2/2007 | Urmey | |
| 2007/0049962 A1 | 3/2007 | Marino | |
| 2007/0184422 A1 | 8/2007 | Takahashi | |
| 2007/0202005 A1 | 8/2007 | Maschke | |
| 2008/0027507 A1 | 1/2008 | Bijelic | |
| 2008/0058606 A1 | 3/2008 | Miles | |
| 2008/0065144 A1 | 3/2008 | Marino | |
| 2008/0071191 A1 | 3/2008 | Kelleher | |
| 2008/0082136 A1 | 4/2008 | Gaudiani | |
| 2008/0097164 A1 | 4/2008 | Miles | |
| 2008/0108244 A1 | 5/2008 | Jepsen | |
| 2008/0167574 A1 | 7/2008 | Farquhar | |
| 2008/0183096 A1 | 7/2008 | Snyder | |
| 2008/0194970 A1 | 8/2008 | Steers | |
| 2008/0269777 A1 | 10/2008 | Appenrodt | |
| 2008/0281313 A1 | 11/2008 | Fagin | |
| 2008/0312520 A1 | 12/2008 | Rowlandson | |
| 2009/0018399 A1 | 1/2009 | Martinelli | |
| 2009/0088660 A1 | 4/2009 | McMorrow | |
| 2009/0105604 A1 | 4/2009 | Bertagnoli | |
| 2009/0177112 A1 | 7/2009 | Gharib | |
| 2009/0196471 A1 | 8/2009 | Goetz | |
| 2009/0204016 A1 | 8/2009 | Gharib | |
| 2009/0209879 A1 | 8/2009 | Kaula | |
| 2009/0259108 A1 | 10/2009 | Miles | |
| 2009/0279767 A1 | 11/2009 | Kukuk | |
| 2010/0036384 A1 | 2/2010 | Gorek | |
| 2010/0106011 A1 | 4/2010 | Byrd | |
| 2010/0113898 A1 | 5/2010 | Kim | |
| 2010/0152604 A1 | 6/2010 | Kaula | |
| 2010/0168603 A1 | 7/2010 | Himes | |
| 2010/0191305 A1 | 7/2010 | Imran | |
| 2010/0249638 A1 | 9/2010 | Liley | |
| 2010/0286554 A1 | 11/2010 | Davis | |
| 2010/0317931 A1 | 12/2010 | Sarkela | |
| 2010/0317989 A1 | 12/2010 | Gharib | |
| 2011/0082383 A1 | 4/2011 | Cory | |
| 2011/0184308 A1 | 7/2011 | Kaula | |
| 2011/0295579 A1 | 12/2011 | Tang | |
| 2011/0313530 A1 | 12/2011 | Gharib | |
| 2012/0003862 A1 | 1/2012 | Newman | |
| 2012/0071779 A1 | 3/2012 | Sarkela | |
| 2012/0109000 A1 | 5/2012 | Kaula | |
| 2012/0109004 A1 | 5/2012 | Cadwell | |
| 2012/0209082 A1 | 8/2012 | Al-Ali | |
| 2012/0209346 A1* | 8/2012 | Bikson | A61N 1/3603 607/45 |
| 2012/0220891 A1 | 8/2012 | Kaula | |
| 2012/0238893 A1 | 9/2012 | Farquhar | |
| 2012/0265040 A1 | 10/2012 | Ito | |
| 2012/0296230 A1 | 11/2012 | Davis | |
| 2013/0012880 A1 | 1/2013 | Blomquist | |
| 2013/0109996 A1 | 5/2013 | Turnbull | |
| 2013/0138010 A1 | 5/2013 | Nierenberg | |
| 2013/0152657 A1 | 6/2013 | Swinehart | |
| 2013/0204315 A1* | 8/2013 | Wongsarnpigoon | A61N 1/361 607/45 |
| 2013/0304407 A1 | 11/2013 | George | |
| 2014/0121555 A1 | 5/2014 | Scott | |
| 2014/0275926 A1 | 9/2014 | Scott | |
| 2014/0276181 A1 | 9/2014 | Sun | |
| 2015/0230749 A1 | 8/2015 | Gharib | |
| 2015/0351643 A1 | 12/2015 | Edwards | |
| 2015/0372433 A1 | 12/2015 | Lisogurski | |
| 2016/0000382 A1 | 1/2016 | Jain | |
| 2016/0174861 A1 | 6/2016 | Cadwell | |
| 2016/0328991 A1 | 11/2016 | Simpson | |
| 2018/0117309 A1 | 5/2018 | Rapoport | |
| 2018/0161123 A1 | 6/2018 | Cadwell | |
| 2018/0198218 A1 | 7/2018 | Regan | |
| 2018/0256097 A1* | 9/2018 | Bray | A61B 5/296 |
| 2018/0296277 A1* | 10/2018 | Schwartz | A61B 18/1492 |
| 2019/0190187 A1 | 6/2019 | Fukazawa | |
| 2020/0108246 A1* | 4/2020 | Cadwell | A61N 1/0539 |
| 2020/0330772 A1 | 10/2020 | Hartmann-Bax | |

FOREIGN PATENT DOCUMENTS

| | | |
|---|---|---|
| EP | 0863719 A1 | 9/1998 |
| EP | 890341 | 1/1999 |
| EP | 972538 | 1/2000 |
| EP | 1182965 B1 | 3/2002 |
| EP | 2173238 A2 | 4/2010 |
| WO | 2000038574 A1 | 7/2000 |
| WO | 2000066217 A1 | 11/2000 |
| WO | 2001037728 A1 | 5/2001 |
| WO | 2003005887 A2 | 1/2003 |
| WO | 2005030318 A1 | 4/2005 |
| WO | 2006042241 A2 | 4/2006 |
| WO | 2016028822 A1 | 2/2016 |

OTHER PUBLICATIONS

Clements, et. al., "Evoked and Spontaneous Electromyography to Evaluate Lumbosacral Pedicle Screw Placement", 21 (5):600-604 (1996).

Danesh-Clough, et. al., "The Use of Evoked EMG in Detecting Misplaced Thoracolumbar Pedicle Screws", 26(12):1313-1316 (2001).

Dezawa et al., "Retroperitoneal Laparoscopic Lateral Approach to the Lumbar Spine: A New Approach, Technique, and Clinical Trial", Journal of Spinal Disorders 13(2):138-143 (2000).

Dickman, et al., "Techniques in Neurosurgery", National Library of Medicine, 3 (4) 301-307 (1997).

Epstein, et al., "Evaluation of Intraoperative Somatosensory—Evoked Potential Monitoring During 100 Cervical Operations", 18(6):737-747 (1993), J.B. Lippincott Company.

Glassman, et. al., "A Prospective Analysis of Intraoperative Electromyographic Monitoring of Pedicle Screw Placement with Computed Tomographic Scan Confirmation", 20(12):1375-1379.

Goldstein, et. al., "Minimally Invasive Endoscopic Surgery of the Lumbar Spine", Operative Techniques in Orthopaedics, 7 (1):27-35 (1997).

Greenblatt, et. al., "Needle Nerve Stimulator-Locator", 41 (5):599-602 (1962).

H.M. Mayer, "Minimally Invasive Spine Surgery, A Surgical Manual", Chapter 12, pp. 117-131 (2000).

(56) References Cited

OTHER PUBLICATIONS

Hinrichs, et al., "A trend-detection algorithm for intraoperative EEG monitoring", Med. Eng. Phys. 18 (8):626-631 (1996).
Bergey et al., "Endoscopic Lateral Transpsoas Approach to the Lumbar Spine", SPINE 29 (15):1681-1688 (2004).
Holland, "Spine Update, Intraoperative Electromyography During Thoracolumbar Spinal Surgery", 23 (17):1915-1922 (1998).
Holland, et al., "Continuous Electromyographic Monitoring to Detect Nerve Root Injury During Thoracolumbar Scoliosis Surgery", 22 (21):2547-2550 (1997), Lippincott-Raven Publishers.
Hovey, A Guide to Motor Nerve Monitoring, pp. 1-31, Mar. 20, 1998, The Magstim Company Limited.
Kevin T. Foley, et. al., "Microendoscipic Discectomy" Techniques in Neurosurgery, 3:(4):301-307, © 1997 Lippincott-Raven Publishers, Philadelphia.
Kossmann et al., "The use of a retractor system (SynFrame) for open, minimal invasive reconstruction of the anterior column of the thoracic and lumbar spine", 10:396-402 (2001).
Kossmann, et. al., "Minimally Invasive Vertebral Replacement with Cages in Thoracic and Lumbar Spine", European Journal of Trauma, 2001, No. 6, pp. 292-300.
Lenke, et. al., "Triggered Electromyographic Threshold for Accuracy of Pedicle Screw Placement, An Animal Model and Clinical Correlation", 20 (14):1585-1591 (1995).
Lomanto et al., "7th World Congress of Endoscopic Surgery" Singapore, Jun. 1-4, 2000 Monduzzi Editore S.p.A.; email: monduzzi@monduzzi.com, pp. 97-103 and 105-111.
MaGuire, et. al., "Evaluation of Intrapedicular Screw Position Using Intraoperative Evoked Electromyography", 20 (9):1068-1074 (1995).
Mathews et al., "Laparoscopic Discectomy With Anterior Lumbar Interbody Fusion, A Preliminary Review", 20 (16):1797-1802, (1995), Lippincott-Raven Publishers.
Bertagnoli, et. al., "The AnteroLateral transPsoatic Approach (ALPA), A New Technique for Implanting Prosthetic Disc-Nucleus Devices", 16 (4):398-404 (2003).
Michael R. Isley, et. al., "Recent Advances in Intraoperative Neuromonitoring of Spinal Cord Function: Pedicle Screw Stimulation Techniques", Am. J. End Technol. 37:93-126 (1997).
Minahan, et. al., "The Effect of Neuromuscular Blockade on Pedicle Screw Stimulation Thresholds" 25(19):2526-2530 (2000).
Pimenta et. al., "Implante de prótese de núcleo pulposo: análise inicial", J Bras Neurocirurg 12 (2):93-96, (2001).
Raymond J. Gardocki, MD, "Tubular diskectomy minimizes collateral damage", AAOS Now, Sep. 2009 Issue, http://www.aaos.org/news/aaosnow/sep09/clinical12.asp.
Raymond, et. al., "The NerveSeeker: A System for Automated Nerve Localization", Regional Anesthesia 17:151-162 (1992).
Reidy, et. al., "Evaluation of electromyographic monitoring during insertion of thoracic pedicle screws", British Editorial Society of Bone and Joint Surgery 83 (7):1009-1014, (2001).
Rose et al., "Persistently Electrified Pedicle Stimulation Instruments in Spinal Instrumentation: Technique and Protocol Development", Spine: 22(3): 334-343 (1997).
Teresa Riordan "Patents; A businessman invents a device to give laparoscopic surgeons a better view of their worK", New York Times www.nytimes.com/2004/29/business/patents-businessman-invents-device-give-la (Mar. 2004).
Toleikis, et. al., "The usefulness of Electrical Stimulation for Assessing Pedicle Screw Placements", Journal of Spinal Disorders, 13 (4):283-289 (2000).
U.Schick, et. al., "Microendoscopic lumbar discectomy versus open surgery: an intraoperative EMG study", pp. 20-26, Published online: Jul. 31, 2001 © Springer-Verlag 2001.

Bose, et. al., "Neurophysiologic Monitoring of Spinal Nerve Root Function During Instrumented Posterior Lumbar Spine Surgery", 27 (13):1440-1450 (2002).
Vaccaro, et. al., "Principles and Practice of Spine Surgery", Mosby, Inc. ©2003, Chapter 21, pp. 275-281.
Vincent C. Traynelis, "Spinal arthroplasty", Neurosurg Focus 13 (2):1-7. Article 10, (2002).
Welch, et. al., "Evaluation with evoked and spontaneous electromyography during lumbar instrumentation: a prospective study", J Neurosurg 87:397-402, (1997).
Zouridakis, et. al., "A Concise Guide to Intraoperative Monitoring", Library of Congress card No. 00-046750, Chapter 3, p. 21, chapter 4, p. 58 and chapter 7 pp. 119-120.
Medtronic, "Nerve Integrity Monitor, Intraoperative EMG Monitor, User's Guide", Medtronic Xomed U.K. Ltd., Unit 5, West Point Row, Great Park Road, Almondsbury, Bristol B5324QG, England, pp. 1-39.
Chapter 9, "Root Finding and Nonlinear Sets of Equations", Chapter 9:350-354, http://www.nr.com.
Digitimer Ltd., 37 Hydeway, Welwyn Garden City, Hertfordshire. AL7 3BE England, email:sales@digitimer.com, website: www.digitimer.com, "Constant Current High Voltage Stimulator, Model DS7A, For Percutaneous Stimulation of Nerve and Muscle Tissue".
Ford et al, Electrical characteristics of peripheral nerve stimulators, implications for nerve localization, Dept. of Anesthesia, University of Cincinnati College of Medicine, Cincinnati, OH 45267, pp. 73-77.
Deletis et al., "The role of intraoperative neurophysiology in the protection or documentation of surgically induced injury to the spinal cord", Correspondence Address: Hyman Newman Institute for Neurology & Neurosurgery, Beth Israel Medical Center, 170 East End Ave., Room 311, NY 10128.
Urmey "Using the nerve stimulator for peripheral or plexus nerve blocks" Minerva Anesthesiology 2006; 72:467-71.
Butterworth et. al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.
Calancie, et. al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).
Calancie, et. al., "Threshold-level repetitive transcranial electrical stimulation for intraoperative monitoring of central motor conduction", J. Neurosurg 95:161-168 (2001).
Calancie, et. al., Stimulus-Evoked EMG Monitoring During Transpedicular Lumbosacral Spine Instrumentation, Initial Clinical Results, 19 (24):2780-2786 (1994).
Carl T. Brighton, "Clinical Orthopaedics and Related Research", Clinical Orthopaedics and related research No. 384, pp. 82-100 (2001).
International Search Report for PCT/US2019/063793, dated Feb. 19, 2020.
International Search Report for PCT/US2017/062559, dated Jan. 26, 2018.
Brainstorm Website, http://neuroimage.usc.edu/brainstorm/ accessed online Oct. 9, 2021, available online Apr. 11, 2018. (Year: 2018).
Compumedics Website, "Compumedics Profusion EEG 4" accessed online Oct. 9, 2021, available online Feb. 23, 2017 (ttps://www.compumedics.com.au/wp-content/uploads/2016/08/AD125-02-Profusion-EEG4-brochureLR.pdf (Year:2017).
Intelimed Website, "Compumedics Profusion EEG 5 Top Features" accessed online Oct. 9, 2021, available online Sep. 30, 2014 2014).

\* cited by examiner

METHOD AND SYSTEM FOR ELECTRODE VERIFICATION

CROSS REFERENCE

The present application relies on U.S. Patent Provisional Application No. 62/767,504, entitled "Method and System for Electrode Verification" and filed on Nov. 14, 2018, for priority, which is herein incorporated by reference in its entirety.

FIELD

The present specification generally relates to the field of neuro-monitoring applications and more specifically to a system and method for managing a large number of electrodes in such applications.

BACKGROUND

Several medical procedures involve deploying multiple sensors on the human body for the recording and monitoring of data required for patient care. Information, such as vital health parameters, cardiac activity, bio-chemical activity, electrical activity in the brain, gastric activity and physiological data, is usually recorded through on-body or implanted sensors/electrodes which are controlled through a wired or wireless link. Typical patient monitoring systems comprise a control unit connected through a wire to one or more electrodes coupled to the specific body parts of the patient. In some applications, such as with pulse oximeter or EKG (electrocardiograph) devices, the electrodes coupled to the body are easily managed as there are not too many (fewer number of electrodes). However, with applications that require a large number of electrodes to be coupled to the human body, the overall set up, placement and management of electrodes is a cumbersome process.

Neuromonitoring is the use of electrophysiological methods, such as electroencephalography (EEG), electromyography (EMG), and evoked potentials, to monitor the function of certain neural structures (e.g., nerves, spinal cord and brain) during surgery. Neuromonitoring is used to reduce the risk to the patient of iatrogenic damage to the nervous system, to provide functional guidance to the surgeon and anesthesiologist, and to observe normal and abnormal neural activity both during and post surgery, locating anatomical sites of such activity and to determine if those sites present special risks from a proposed therapy. Generally, neuromonitoring procedures such as EEG involve a large number of electrodes coupled to the human body. In an EEG procedure, the electrodes are used to record and monitor the electrical activity corresponding to various parts of the brain for detection and treatment of various ailments such as epilepsy, sleep disorders and coma. EEG procedures are either non-invasive or invasive. In non-invasive EEG, a number of electrodes are deployed on the human scalp for recording electrical activity in portions of the underlying brain. In invasive EEG, through surgical intervention, the electrodes are placed directly over sections of the brain, in the form of a strip or grid, or are positioned in the deeper areas of the brain. Each of these electrodes is coupled to a wire lead which, in turn, is connected to a control unit adapted to receive and transmit electrical signals. The electrical activity pattern captured by various electrodes is analyzed using standard algorithms to localize or spot the portion of brain which is responsible for causing the specific ailment.

The number of electrodes in EEG systems typically varies between 21 to greater than 256. Increasing the number of electrodes in EEG procedures helps decrease the localization error and thus more ably assist the physician to better plan for surgical procedures. Accordingly, advanced EEG systems involve a high density electrode configuration with 256 or more electrodes for separately mapping the electrical activity corresponding to smaller portions of the brain. However, the overall set up and verification process becomes more time consuming and error prone as the number of electrodes increases in the EEG procedures.

In neuromonitoring, as each electrode is positioned at a different location to capture the electrical activity in its vicinity, the input recorded from each electrode has to be processed independently. The system is required to recognize the identity of each electrode and accordingly process the input received from that electrode. To achieve this, it is important that each electrode is coupled to the correct input channel in the control unit of the neuromonitoring system. However, in practical scenarios, it is possible that, while connecting a large number of electrodes to respective input channels, the medical care provider connects an electrode to a wrong input channel. This could result in making the entire process faulty.

The problem of misconnection is currently mitigated by careful and meticulous placement of each electrode, then having the locations verified by a second person. This is a tedious, time-consuming and expensive process. In practice, the time required to set up and verify large numbers of connecting leads can prevent following the best practice of checking all electrodes and verifying their integrity before starting the procedure and hence compromises the quality of medical care.

Surgical applications in EEG also use grid electrodes which inherently combine multiple leads (typically 8 to 32) into a single connector, which is then attached to an adapter with the same number of individual leads, and then to an amplifier that has inputs for each individual channel. However, when a patient is monitored with an EEG system having 200+ electrodes, even grouping these electrodes results in more than a dozen adapters and the connections corresponding to these adapters needs to be individually verified every time before starting a procedure. The currently used processes also fail to detect a grid or depth electrode that may have been improperly wired, and because there are multiple groups of electrodes, an entire bank could be inadvertently swapped with a different bank.

Therefore, the current neuromonitoring medical devices involving a large number of electrodes do not provide an easy and convenient way for physicians to deploy such systems. These systems suffer from significant risk of unreliable measurements due to incorrect connections. There is significant risk of error in deploying such systems. Further, deployment of such systems is time consuming which prevents following the best practices and therefore compromises the quality of medical care. Broken leads or electrodes that are not making good electrical contact are also problems that reduce the quality and reliability of a study. Detecting bad electrodes and either removing them from the analysis or fixing the problem is beneficial.

FIG. 1A shows a block diagram of a conventional medical system 100 comprising a large number of electrodes deployed on a patient 102 body. The medical device 101 represents any conventional neuromonitoring medical system which comprises a large number of electrodes, such as an EEG (electroencephalography) system, which is used for monitoring the neurological state of a patient for diagnosis and preventive treatment of certain diseases and for monitoring patients during anesthesia, among other procedures. As shown in FIG. 1A, the medical device 101 is coupled to the patient 102 through a plurality of electrical leads 103 such that each of the leads 103 is coupled to an electrode (not shown) positioned at an appropriate location on the body of the patient. In applications that require a large number of electrodes to be coupled to the human body, the setup, placement and management of electrodes is a cumbersome process. As each electrode is positioned at a different location to capture the electrical activity in its vicinity, the input recorded from each electrode has to be processed independently. Therefore, the system is required to recognize the identity of each of the electrical leads 103 and accordingly process the input received from it. After positioning any electrode at its required location on the body of the patient 102, the user is required to correctly insert the electrode lead 103 corresponding to each electrode in a specific input channel configured for that electrode in the medical device 101. In case the number of electrodes is small, for example, less than ten or fifteen, it is possible for the user to identify and connect electrodes with the correct input channels. However, as the number of electrodes increases, this process become very difficult and is prone to error. Further, even if the electrodes are coupled to the correct input slots in the medical device 101, it is practically very difficult and time consuming to recheck and verify the integrity of each connection before every procedure. Usually, in such high density configurations, the set up process is so time consuming that in some circumstances, for example during a surgical procedure, the user completely or partially skips the step of checking each connection for integrity until after the surgery is finished, which increases the possibility of error in the procedure.

Therefore, there is a need to reliably and accurately verify electrode locations and integrity after the connections have been made. There is also a need for devices and processes which are convenient to use and do not consume too much time for deployment. Such devices and processes should automatically recognize the position or identity of various electrodes and associate the electrodes with a specific input channel, thereby not requiring the physician to manually map each electrode with a specific input channel.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a method for verification of location of electrodes in a neuromonitoring system, the method comprising: injecting a known signal, wherein the signal comprises a normal and a reverse polarity that are respectively input to a first electrode and a second electrode, wherein the first electrode and the second electrode are surrounded by a plurality of neighboring electrodes, and wherein the injecting the signal generates an electric field around the first electrode, the second electrode, and the plurality of neighboring electrodes; measuring concurrent responses to the electric field at the plurality of neighboring electrodes, wherein the measuring comprises measuring amplitude, polarity, and waveform of the responses; measuring baseline noise at the first electrode, the second electrode, and the plurality of neighboring electrodes, before and after the injecting the signal; determining expected responses to the signal, at the plurality of neighboring electrodes for the expected geometry of the first electrode, the second electrode, and the plurality of neighboring electrodes; comparing the measured concurrent responses to the expected responses; flagging the one or more of the electrodes of the plurality of neighboring electrodes for which the comparing determines that the measured response is different from the expected response, wherein the flagging indicates an incorrect location of the flagged electrodes; and displaying at least the flagged electrodes.

Optionally, the first electrode, the second electrode, and the plurality of neighboring electrodes form an electrode group, each of said electrodes in the group having at least one of a similar monitoring functionality and a similar deployment location.

Optionally, the first electrode and the second electrode are extracranial electrodes and the plurality of neighboring electrodes are at least one of intracranial electrodes or extracranial electrodes.

Optionally, the first electrode, the second electrode, and the electrodes of the plurality of neighboring electrodes are intracranial electrodes.

Optionally, the electrodes are at least one of a group of grid electrodes, strip electrodes, and depth electrodes.

Optionally, the first electrode, the second electrode, and the electrodes of the plurality of neighboring electrodes comprise both extracranial electrodes and intracranial electrodes.

Optionally, said method further comprises determining whether the flagged electrodes are misconnected.

Optionally, the method further comprises displaying the misconnected electrodes.

Optionally, the displaying comprises displaying at least one of a graph and a table, wherein displaying distinguishes the flagged electrodes from the remaining of the first electrode, the second electrode, and the electrodes of the plurality of neighboring electrodes.

Optionally, the comparing comprises: assigning the electrodes of the plurality of neighboring electrodes a weight based on their position relative to the first electrode and the second electrode; and considering the assigned weights during the comparing.

Optionally, the method further comprises repeating the method while injecting the signal to a different combination of electrodes from the group of the first electrode, the second electrode, and the plurality of neighboring electrodes; evaluating the flagged electrodes identified from each repetition, wherein the evaluating comprises performing a statistical evaluation; and verifying location of the first electrode, the second electrode, and the electrodes of the plurality of neighboring electrodes, based on the evaluating.

The present specification also discloses a system for neuromonitoring comprising: a first electrode; a second electrode; a plurality of neighboring electrodes, wherein the electrodes of the plurality of neighboring electrodes are located on a same side, front, or back of a patient's head, scalp, or brain as the first electrode and the second electrode for neuromonitoring and wherein the first electrode and the second electrode are surrounded by the plurality of neighboring electrodes; a signal generator to generate voltage signals for injecting to the first electrode and the second electrode, wherein the injecting generates an electric field around the first electrode, the second electrode, and the plurality of neighboring electrodes; an amplifier connected to each of the first electrode, the second electrode, and the plurality of neighboring electrodes, wherein the amplifier is configured to receive responses to the signals generated by the signal generator, convert the responses from analog to digital format, and transmit the responses; a control unit configured for: receiving the responses transmitted by the amplifier; measuring the responses to the electric field at the plurality of neighboring electrodes; measuring baseline noise at the first electrode, the second electrode, and the plurality of neighboring electrodes, before and after the injecting the signal; determining expected responses to the signal, at the plurality of neighboring electrodes for the expected geometry of the first electrode, the second electrode, and the plurality of neighboring electrodes; comparing the measured responses to the expected responses; flagging the one or more of the electrodes of the plurality of neighboring electrodes for which the comparing determines that the measured response is different from the expected response, wherein the flagging indicates an incorrect location of the flagged electrodes; repeating the method while the signal is injected to a different combination of electrodes from the group of the first electrode, the second electrode, and the plurality of neighboring electrodes; evaluating the flagged electrodes identified from each repetition, wherein the evaluating comprises performing a statistical evaluation; and verifying location of the first electrode, the second electrode, and the plurality of neighboring electrodes, based on the evaluating; and a display for displaying at least the flagged electrodes.

Optionally, the first electrode, the second electrode, and the plurality of neighboring electrodes form an electrode group, each of said electrodes in the group having at least one of a similar monitoring functionality and a similar deployment location.

Optionally, the first electrode and the second electrode are extracranial electrodes and the electrodes of the plurality of neighboring electrodes are at least one of intracranial electrodes or extracranial electrodes.

Optionally, the first electrode, the second electrode, and the electrodes of the plurality of neighboring electrodes are intracranial electrodes. Optionally, the electrodes are at least one of a group of grid electrodes, strip electrodes, and depth electrodes.

Optionally, the first electrode, the second electrode, and the electrodes of the plurality of neighboring electrodes comprise both extracranial electrodes and intracranial electrodes.

Optionally, said control unit is further configured for determining whether the flagged electrodes are misconnected. Optionally, the display is configured to display the misconnected electrodes.

Optionally, the display is further configured for displaying at least one of a graph and a table, wherein the displaying distinguishes the flagged electrodes from the remaining of the first electrode, the second electrode, and the electrodes of the plurality of neighboring electrodes. The aforementioned and other embodiments of the present shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings.

DETAILED DESCRIPTION

Figure 1A:
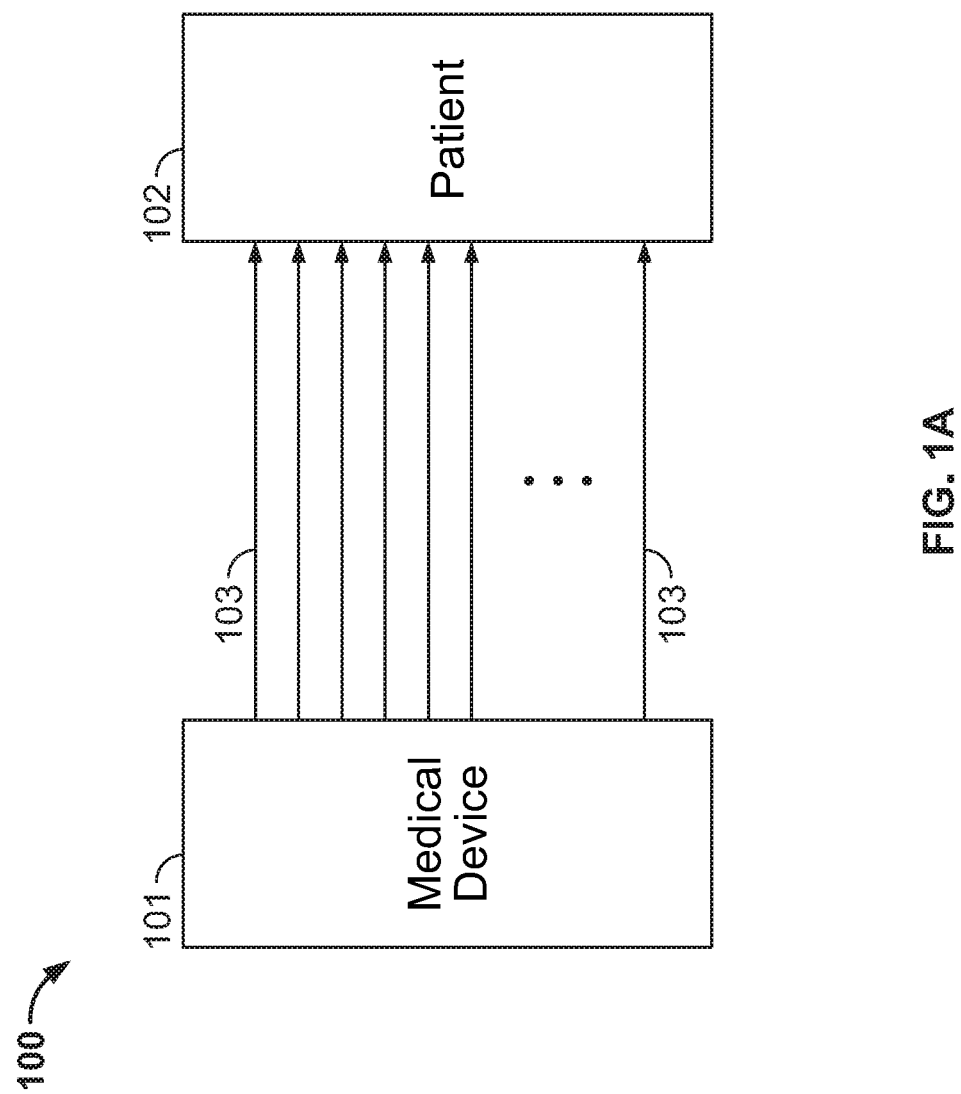
FIG. 1A shows a block diagram of a conventional medical system comprising a large number of electrodes deployed on a patient body.

The system, devices, and methods described below disclose a novel electrode management solution for neuromonitoring applications such as electroencephalography (EEG) procedures. Systems and methods are disclosed which provide a highly reliable and convenient method for electrode management in such applications. In embodiments of the disclosed system, the physician is not required to manually verify the match of each electrode lead with its corresponding input channel on the system control unit, significantly reducing the set up time.

The desired electrode locations are usually well defined and may be on the surface of the scalp, in or on the brain, or at some other location on the body. Depth electrodes and grids consist of multiple electrodes in a matrix, and the expected geometric relation of each input to all other inputs within the matrix is known. In complex cases with multiple grids or multiple depth electrodes, the locations of each individual or group of electrodes is either part of the surgical planning or is noted during the surgery.

In embodiments, the brain is modeled as a volume conductor. If an electrical signal is present in the form of an electrical dipole, the expected attenuated signal generated by this dipole at any other point in the brain is calculated. In embodiments of the present specification, a known signal is connected between electrodes at 'presumed' locations. This action generates a defined electrical field which can be measured between any of the other electrode locations. The amplitude and phase of the measured signals are a function of the input signal, the volume conductor, and the geometric relations of the two electrodes. By comparing the expected values with the measured values, the relation between the electrodes is verified.

In embodiments, a broken lead or high contact resistance is measured using an impedance checking algorithm, and the electrode identified with the broken lead or high contact resistance is flagged. In a case where location is not verified, then either driving electrode(s) or pickup electrodes(s) could be responsible. Therefore, in embodiments, multiple pairs of electrodes are used for both driving and recording. Using multiple combinations provides redundant estimates that either quickly converge or fail to converge if there are problems. The algorithm analyzes multiple results to generate a confidence level about the electrodes assumed versus actual position.

In embodiments, if an electrode is identified to be in a wrong location, its actual correct location is determined using a different algorithm that performs an inverse transform.

The algorithms in accordance with embodiments of the present specification detect multiple misconnects, and also detect entire blocks that are misconnected. Further, the algorithms determine relations between surface electrodes (whose location can be visualized) and cortical electrodes which are hidden after surgery. If the surface electrodes are correctly placed and the placement is verified, then the location of the hidden cortical electrodes relative to the surface electrodes is determined.

The term 'user' is used interchangeably to refer to a surgeon, neuro-physician, neuro-surgeon, neuro-physiologist, technician or operator of the EEG system and/or other patient-care personnel or staff.

A "computing device" is at least one of a cellular phone, PDA, smart phone, tablet computing device, patient monitor, custom kiosk, or other computing device capable of executing programmatic instructions. It should further be appreciated that each device and monitoring system may have wireless and wired receivers and transmitters capable of sending and transmitting data. Each "computing device" may be coupled to at least one display, which displays information about the patient parameters and the functioning of the system, by means of a GUI. The GUI also presents various menus that allow users to configure settings according to their requirements. The system further comprises at least one processor (not shown) to control the operation of the entire system and its components. It should further be appreciated that the at least one processor is capable of processing programmatic instructions, has a memory capable of storing programmatic instructions, and employs software comprised of a plurality of programmatic instructions for performing the processes described herein. In one embodiment, the at least one processor is a computing device capable of receiving, executing, and transmitting a plurality of programmatic instructions stored on a volatile or non-volatile computer readable medium. In addition, the software comprised of a plurality of programmatic instructions for performing the processes described herein may be implemented by a computer processor capable of processing programmatic instructions and a memory capable of storing programmatic instructions.

"Electrode" refers to a conductor used to establish electrical contact with a nonmetallic part of a circuit. EEG electrodes are small metal discs usually made of stainless steel, tin, gold, platinum, carbon, or silver covered with a silver chloride coating. They are typically placed on the scalp on predetermined locations, but can also be placed as intracranial electrodes directly on the surface of the brain to record electrical activity from the cerebral cortex.

A "subdural electrode grid" is a thin sheet of material with multiple small (roughly less than a couple mm in size) recording electrodes implanted within it. These are placed directly on the surface of the brain and have the advantage of recording the EEG without the interference of the skin, fat tissue, muscle, and bone that may limit scalp EEG. Shapes and sizes of these sheets are chosen to best conform to the surface of the brain and the area of interest.

"Depth Electrode" is an electrode made of thin wires, generally small wires implanted through an invasive procedure into the brain. Each wire has electrodes which surround it. These electrodes are able to record brain activity along the length of the implanted wire. They have the advantage of recording activity from structures deeper in the brain. It is most effectively known to be used to record the electrical activity of structures beneath the cerebral surface, such as the hippocampus. They can be implanted through small cranial holes.

"Grid Electrodes" are electrodes involving placement of a grid of electrodes in the form of multi-contact grids comprising rows and columns of electrodes, usually planted on a thin sheet of plastic, directly on the surface of the brain.

"Strip Electrode" is an electrode in the form of a strip comprising a single row/column of electrodes, such as a thin plastic sheet, and is placed as an intracranial electrode directly of the surface of the brain.

"Montage" refers to the placement or arrangement of the electrodes. The EEG can be monitored with either a bipolar montage or a referential montage. Bipolar means that there are two electrodes per one channel, so there is a reference electrode for each channel. The referential montage means that there is a common reference electrode for all the channels.

Figure 1B:
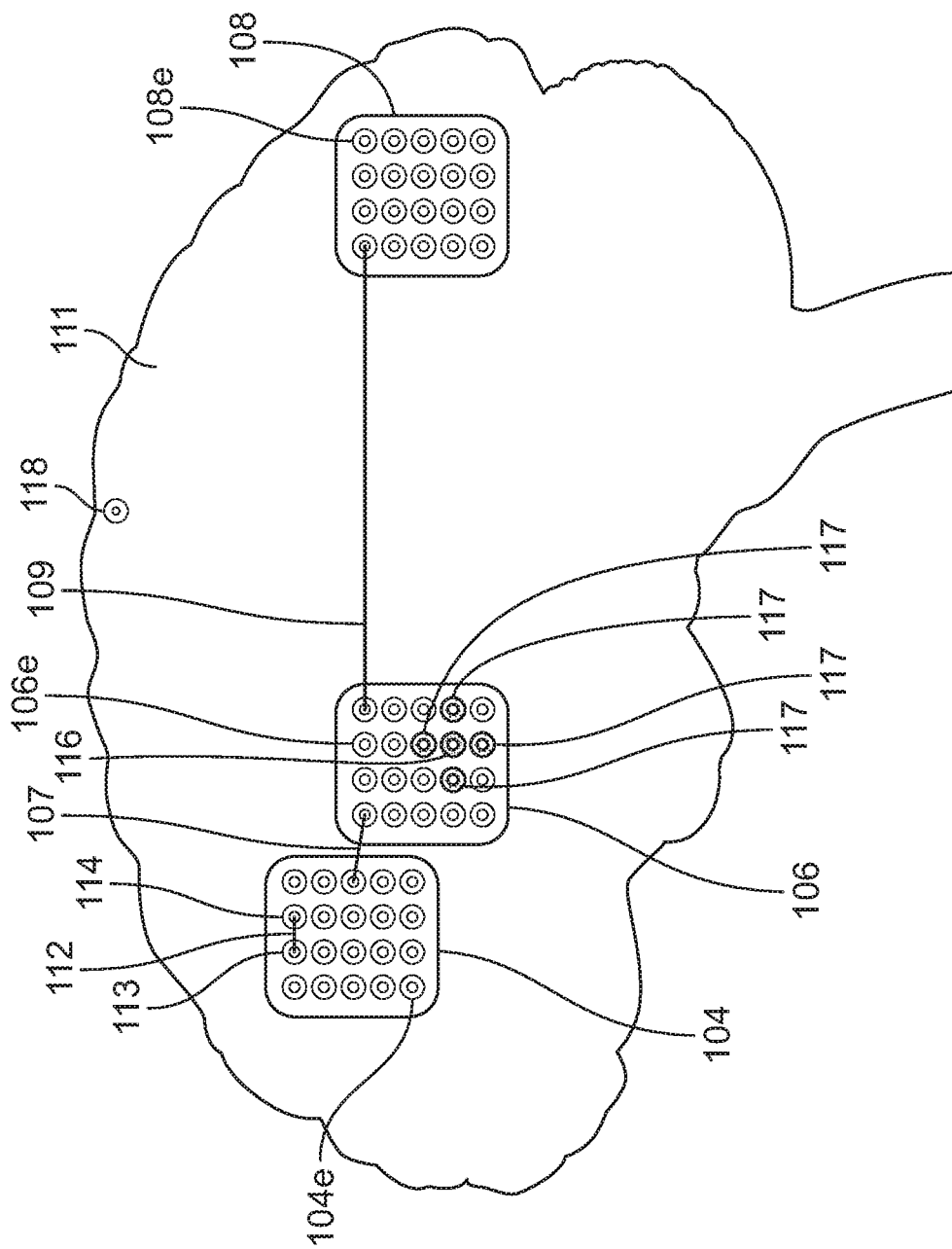
FIG. 1B illustrates a human brain with a plurality of electrode groups deployed thereon, in accordance with embodiments of the present specification.

For purposes of the present specification, the term "similar monitoring functionality" shall mean electrodes that are used for similar neuro-monitoring modalities. For example, electrodes used for studies including, but not limited to, electroencephalography (EEG), electromyography (EMG), and evoked potentials are gathered into groups of similar monitoring functionality. Accordingly, all electrodes being used for an EEG constitute electrodes having a similar monitoring functionality and are expressly differentiated from (and therefore do not have similar monitoring functionality as) those electrodes being used for other modalities, such as an EMG. For purposes of the present specification, the term "similar deployment location" shall mean electrodes that are positioned together in a specific area on or in a patient's head, scalp, or brain. For example, electrodes configured to be placed on a front, back, left side, or right side of a patient's scalp would be gathered into groups of similar deployment location based on each area. Accordingly, all electrodes being deployed in front side of a patient's scalp constitute electrodes having a similar deployment location and are expressly differentiated from (and therefore do not have a similar deployment location as) those electrodes being deployed on the back side, left side, or right side of the patient's scalp, each of those being different deployment locations. This is shown in FIG. 1B, where the electrodes 104e, 106e between the electrode grids or groups 104 and 106 have similar deployment locations on brain 111 because distance 107 is small, and the electrodes 108e of electrode grid or group 108 have dissimilar deployment locations (relative to the electrodes 104e, 106e of electrode groups 104, 106) because distance 109 is large.

In accordance with embodiments of the present specification, the closest electrodes to any given electrode are defined as "neighboring electrodes". Referring to FIG. 1B, the electrodes 113, 114 separated by distance 112 are neighboring electrodes to each other, and electrode 116 is shown with four neighboring electrodes 117. Electrode position can be determined more accurately for electrodes that are closer together because the measured electric field is larger. Verifying that "neighboring electrode" relative positions are correct is done before attempting to verify relations among electrodes that have "dissimilar deployment". For example, the relations of electrodes 104e within grid or group 104 can be verified accurately, but the relation of electrodes 104e in grid or group 104 to electrodes 106e in grid or group 106 is less accurate, and the relation of electrodes 106e in grid or group 106 to electrodes 108e in grid or group 108 is even less accurate.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

An EEG (Electroencephalography) System 110

Figure 1C:
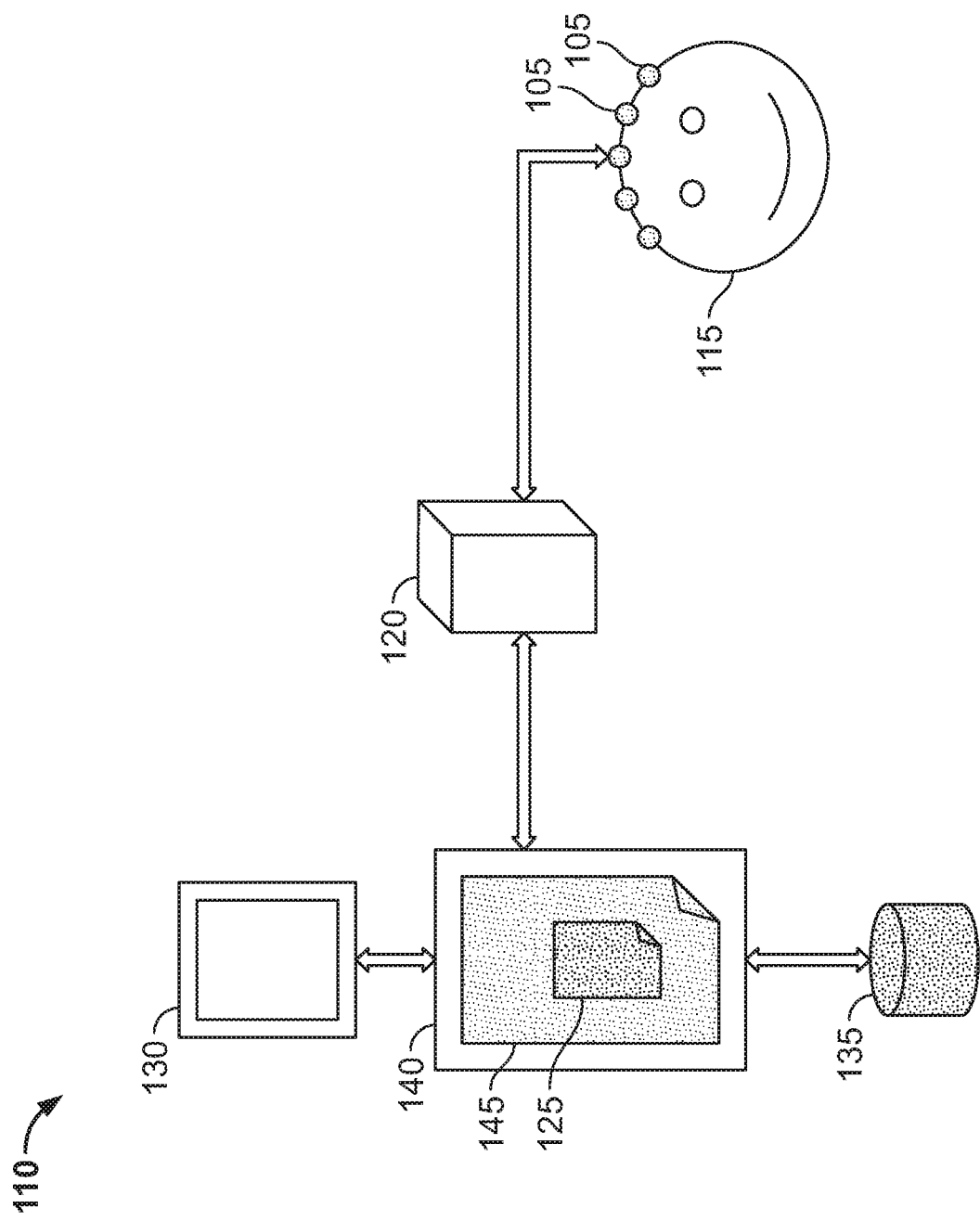
FIG. 1C illustrates an EEG system for detecting, diagnosing, or predicting neurological events from EEG signals, in accordance with some embodiments of the present specification.

FIG. 1C illustrates an EEG system 110 for detecting, diagnosing, or predicting neurological events from EEG signals, in accordance with some embodiments of the present specification. The figure shows a plurality of EEG sensors or electrodes 105 spatially positioned on a layer of tissue such as the scalp of a patient 115. The plurality of electrodes 105 are in data communication with a multi-channel amplifier 120 that is in data communication with a computing device 140. The computing device 140 is in data communication with a display unit 130 and at least one database 135.

In various embodiments, the plurality of electrodes 105 are small metal discs typically made of stainless steel, tin, gold or silver covered with a silver chloride coating. In some embodiments, the plurality of electrodes 105 are placed on the scalp of patient 115. In another embodiment, electrodes 105 are placed as intracranial electrodes as either or a combination of one or more depth electrodes, grid electrodes, and strip electrodes. The plurality of electrodes 105 record electrical signals (EEG signals) from the patient's brain and communicate the analogue signals over a first communication link to the multi-channel amplifier 120 that amplifies the signals, converts the signals from analog to digital, and communicates the resultant digital EEG signal to the computing device 140 over a second communication link. In embodiments, the first and second communication links may be wired or wireless links.

The computing device 140 includes an input/output controller, at least one communications interface and system memory. The system memory includes at least one random access memory (RAM) and at least one read-only memory (ROM). These elements are in communication with a central processing unit (CPU) to enable operation of the computing device 140. In various embodiments, the computing device 140 may be a conventional standalone computer or alternatively, the functions of the computing device 140 may be distributed across multiple computer systems and architectures. For example, in a distributed architecture the at least one database 135 and processing circuitry are housed in separate units or locations. Some units perform primary processing functions and contain at a minimum a general controller or a processing circuitry and a system memory.

The computing device 140 executes EEG software 145 to process, store, retrieve and display, on the display unit 130, the patient's EEG data. In embodiments, the EEG software 145 processes the received signals, extracts parameters that characterize the EEG data, and generates a display of the data for a user. The processed EEG data is either displayed on the display unit 130 in real-time or stored in at least one database 135 for later analyses.

In accordance with an aspect of the present specification, EEG software 145 comprises a module 125 to control signal input to electrodes 105, receive and process digital signals detected and transmitted through amplifier 120, and as a result of processing the signals verify location of electrodes 105. In some embodiments, display unit 130 displays graphically or in tabular format how closely the location calculated by computing device 140, and the expected location, are in agreement. If module 125 detects an error, a graphical presentation that highlights the difference between expected and measured locations are shown through display unit 130. The presentation may allow a user to visualize electrode movement, errors in electrode placement, errors in electrode connection, and electrodes that are not working properly. In some embodiments, the user is also informed about identification of input jacks that may have been misconnected.

In some embodiments, execution of sequences of programmatic instructions enable or cause the CPU to perform various functions and processes. In alternate embodiments, hard-wired circuitry may be used in place of, or in combination with, software instructions for implementation of the processes of systems and methods described in this application. Thus, the systems and methods described are not limited to any specific combination of hardware and software.

Figure 2:
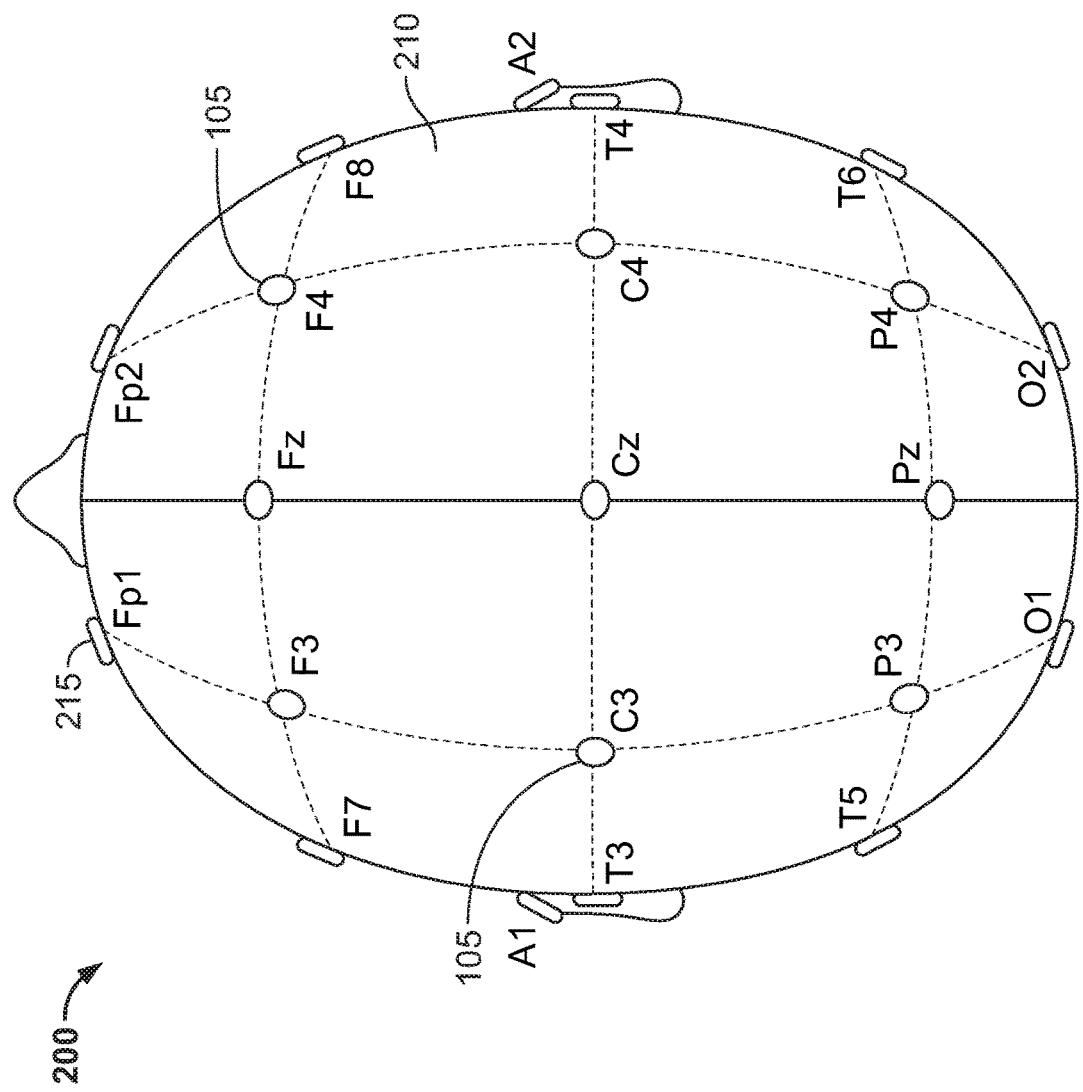
FIG. 2 illustrates a plurality of electrodes that are spatially positioned on a patient's scalp in accordance with the International 10-20 system.

In an embodiment, as shown in FIG. 2, the plurality of electrodes 105 are spatially positioned on the patient's scalp 210 in accordance with the International 10-20 system 200. As known to persons of ordinary skill in the art, the system 200 uses the distance from the bridge of the nose (nasion) to the lowest point of the skull from the back of the head (normally indicated by a prominent bump—the inion) as a reference distance for a given person's head size. The electrodes 105 are then separated from each other either by 10% or 20% of this reference distance. Each electrode placement site has a letter to identify the lobe, or area of the brain it is reading from: Pre-frontal (N), Frontal (F), Temporal (T), Parietal (P), Occipital (O), and Central (C) and a numerical subscript representing position. The midline electrodes are marked with a subscript z, which stands for zero. The odd numbers are used as subscript for points over the left hemisphere and even numbers over the right.

In other embodiments, when greater resolution or granularity is required, the 10-20 system is extended where now the electrodes are separated by 10% of the reference distance (10-10). Further resolution of 5% separation (10-5) distances adds even more electrodes to the scalp. Non-standard montages may be used to increase resolution over particular areas of the brain.

Figure 3:
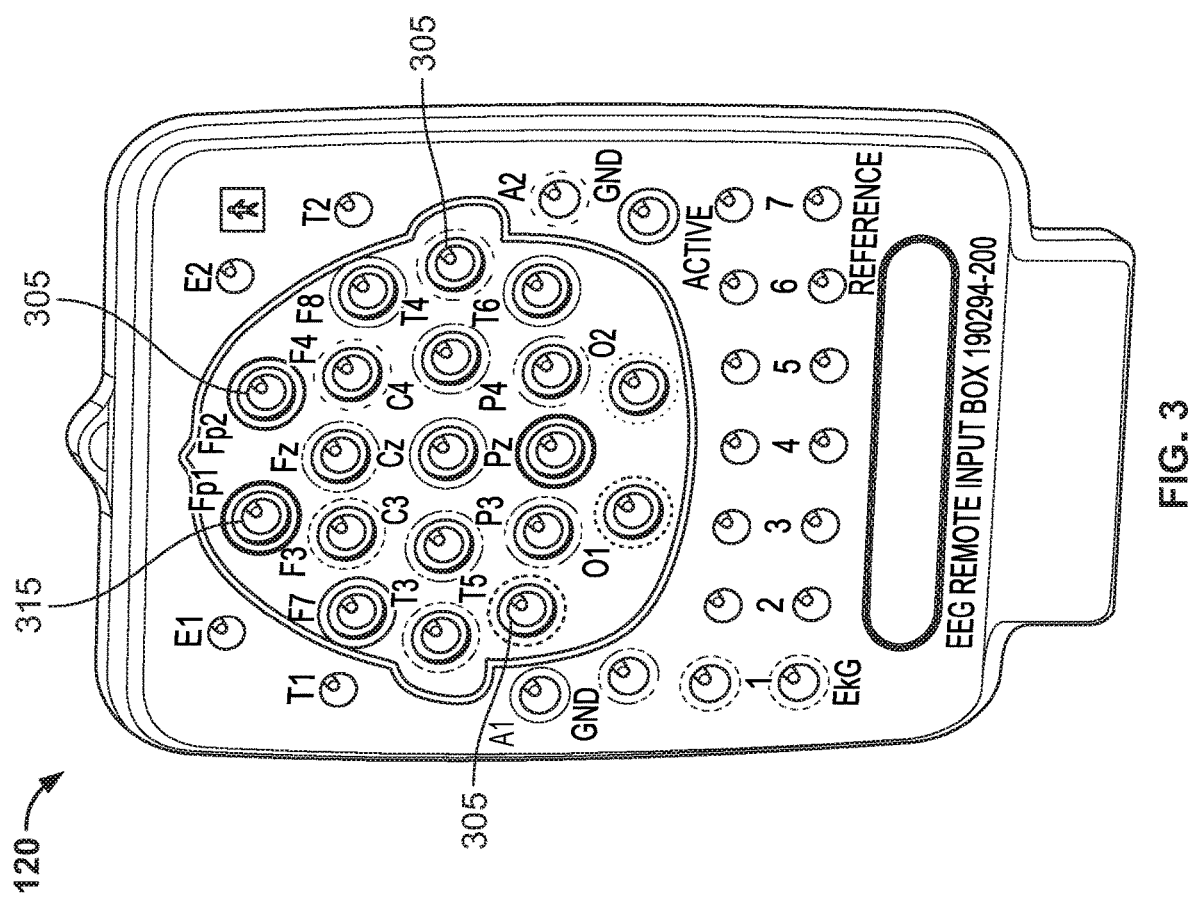
FIG. 3 shows a perspective view of an exemplary multi-channel amplifier, in accordance with some embodiments of the present specification.

FIG. 3 shows a perspective view of an exemplary multi-channel amplifier 120, in accordance with some embodiments of the present specification. The amplifier 120 has a plurality of electrode input channels or ports 305. In accordance with an embodiment, the plurality of input channels or ports 305 are arranged to replicate and correspond to the 10-20 system (system 200 of FIG. 2) of electrode placement on the patient's scalp.

Referring to FIGS. 1C, 2 and 3, in an embodiment, each of the plurality of electrodes 105 (FIG. 1C) is in wired data communication with the corresponding input channel or port 305 identifiable with the respective electrode. For example, an output wire or lead of the electrode Fp1 (referred to as element 215 in FIG. 2) is connected to the corresponding input channel 315 (FIG. 3) on the amplifier 120, and so on. Thus, each recording electrode is uniquely identified and connected to the corresponding uniquely identified input channel or port 305. Consequently, each of the EEG signals acquired by the amplifier 120 is uniquely identified with the associated electrode.

Preparation

In accordance with the various embodiments of the present specification, location of electrodes is verified by injecting signals with specific characteristics, detecting these signals, and comparing the detected signals with the expected signals, thereby indicating any discrepancies in the locations of electrodes. Referring back to FIG. 1C, the electrode location verification module 125 implements a plurality of programmatic instructions to enable a plurality of functions and features, as described in the following paragraphs. Module 125 is provided with information about the electrodes positioned on a patient. The information may comprise types of electrodes 105, such as whether they are positioned on the scalp or are placed intracranially. Information about the type of intracranial electrodes, whether they are depth electrodes, grid electrodes, or strip electrodes, may also be provided. Additionally, expected locations of these electrodes 105 is provided to module 125. This information may be automated to integrate surgical planning tools. The information about the expected location of the electrodes 105 contains a minimum of the body site or 3D position that allows computing relative distances, orientation, and intracranial, extracranial or other location information. Names or references for all electrodes 105 are available to computing device 140, after this step.

Further, electrode connections to amplifier 120 and/or a signal injection system are specified and provided to module 125. This may include individual connections, mass term connections, and ID connections. Individual connections refer to a connection over one wire per one physical connector. Mass term connections refer to one cable of multiple individual wires are terminated at a single connector. The connector is usually rectangular in shape with a double row of contacts. ID connections refer to those described in U.S. patent application Ser. No. 15/376,655, by the Applicant of the present specification, and incorporated herein by reference in its entirety, including any continuations and continuations-in-part therefrom. ID connections connect a group of electrodes with unique identification code stored in an electronically accessible memory. The channel assigned to each electrode is available to computing device 140, after this step.

The process of location verification is executed by module 125. Location verification for a group of electrodes is performed within their group starting with neighboring electrodes. The process of location verification is performed separately for extracranial electrodes. Electrodes 105 are sorted by distance and their neighbors are weighted by proximity and appropriate geometry. Further impedance and/or continuity of each electrode 105 is measured to determine possible misconnections. Electrodes 105 that are identified to be unsuitable for signal injection or pickup, based on the impedance measured in the previous step, are flagged by module 125. Next, a signal is selected or synthesized for injection to electrodes 105. Once the signal is selected, sample rate of the signal is increased if necessary to subsequently capture/detect the injected signal.

Figure 4:
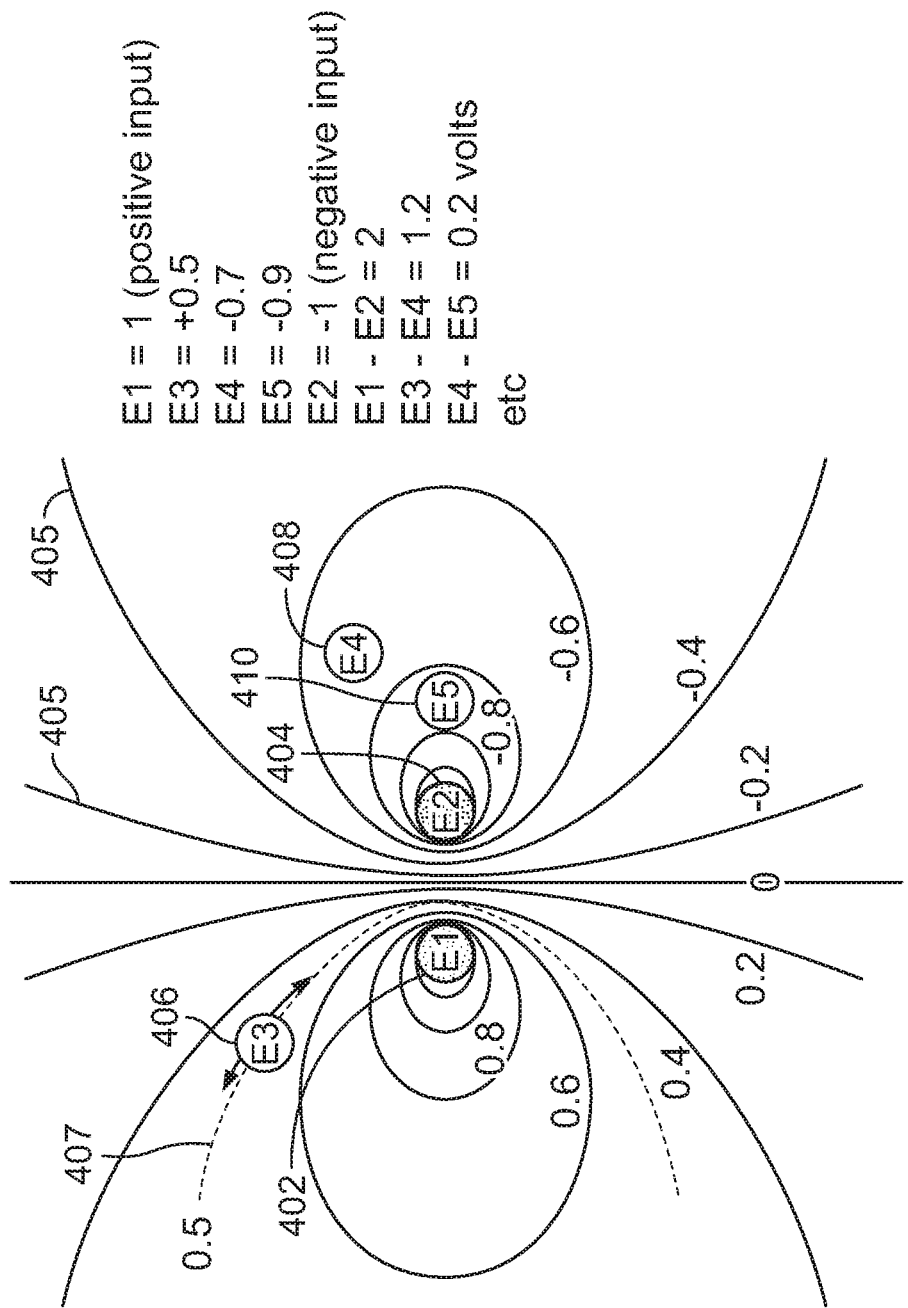
FIG. 4 illustrates an exemplary location of electrodes E1, E2, E3, E4, and E5, in accordance with an embodiment of the present specification, where a signal injected across E1-E2 generates a varying electric field detected by E3, E4 and E5.

FIG. 4 illustrates an exemplary location of electrodes E1, E2, E3, E4, and E5, in accordance with an embodiment of the present specification. Electrode E1 402 is selected for a positive signal injection, and E2 404 is selected for a negative signal injection. In embodiments, signals are measured at electrodes E3 406, E4 408, and E5 410, neighbor electrodes to E1 402 and E2 404.

Injection and Measurement

The injected signals have several characteristics:

1. Low amplitudes that are safe, not able to depolarize neural tissue, and that meet regulatory requirements. For example, direct brain injected signals are typically less than 100 µA and 20-50 µSec duration square waves. Surface electrode injected signals are typically less than 1000 µA and 20-50 µsec duration square waves.
2. Frequencies and/or wave shapes that are easily discernible from the background neural activity (EEG) and other noise sources. For examples, the injected signals include 20-50 µsec pulses or pulse trains.
3. Signals that can be reliably detected by the amplifiers attached to the receiving electrodes.

As would be known to on skilled in the art, an EEG amplifier has a high frequency roll-off and the data acquisition has a sample rate. Fundamental signals and Nyquist aliased signals are detectable and could be part of a detection system.

4. Multiple unique injected signals may be used simultaneously, or a single unique signal may be used sequentially. Another alternative may be to use a mix of these two techniques. If multiple signals are used then multiple results are sorted from each pickup. For a single signal, the results are sorted by time of application.

5. In some embodiments, the resultant signal is large enough to be detected following a single injection. Alternatively, in some embodiments the resultant signal is averaged for detecting. In embodiments, resultant signal may be averaged when multiple unique signals are injected simultaneously.
6. Further, in some embodiments, the injected signals have a switch matrix. The switch matrix consists of two banks of switches. One side of each switch bank is connected to a common input. The two common inputs each connect to one side of the signal injector. The individual contacts of each switch connect to one electrode. Each switch can be individually controlled (on or off) which then allows them to be connected in multiple combinations. For example, any of the contacts may be connected singly or multiply to the either side of the injector circuitry. Thus any contact or group of contacts may be used at different times.
7. In some embodiments, the injected signals may be time synchronized with the recording device. Synchronization allows the recording device to measure the response during the time when the response is expected for a specific injected signal.
8. In some embodiments, the injected signal may be intentionally aliased by increasing its frequency and reducing the patient's brain's ability to respond to the higher frequency, but still allowing detection by the digital sampling system, which, in an embodiment, is part of module 125. Aliasing is done by generating a signal above the Nyquist frequency (which is half the sample rate). The signal would typically be a train of pulses or a periodic wave whose repetition rate is near but not exactly 2n×Nyquist.

Referring again to FIG. 4, once a signal is injected to E1 402 (positive input) and E2 404 (negative input), an electric field 405 is generated around the electrodes 402, 404. The electric field 405 is shown in the form of solid lines. In the illustrated embodiment, voltage at E1 402 is 1V and voltage at E2 404 is −1V. Voltages that may be measured include voltages when an indifferent electrode (one at a great distance that is essentially at 0 volts) is used. An indifferent electrode is shown in FIG. 1B as electrode 118 and could be a cortical or scalp electrode. The voltages measured at the neighboring electrodes E3 406, E4 408, and E5 410 are also shown. In the embodiment, E3 406 is at +0.5V, E4 408 is at −0.7V, and E5 410 is at −0.9V. The voltages measured across any combination of electrodes is the algebraic difference of the voltages at the two electrodes. For example, the difference between E3 406 and E4 408 is 1.2V. However, E3 406 could be anywhere along the 0.5 dashed field line 407 shown in the figure and would give the same result (1.2V).

Figure 5:
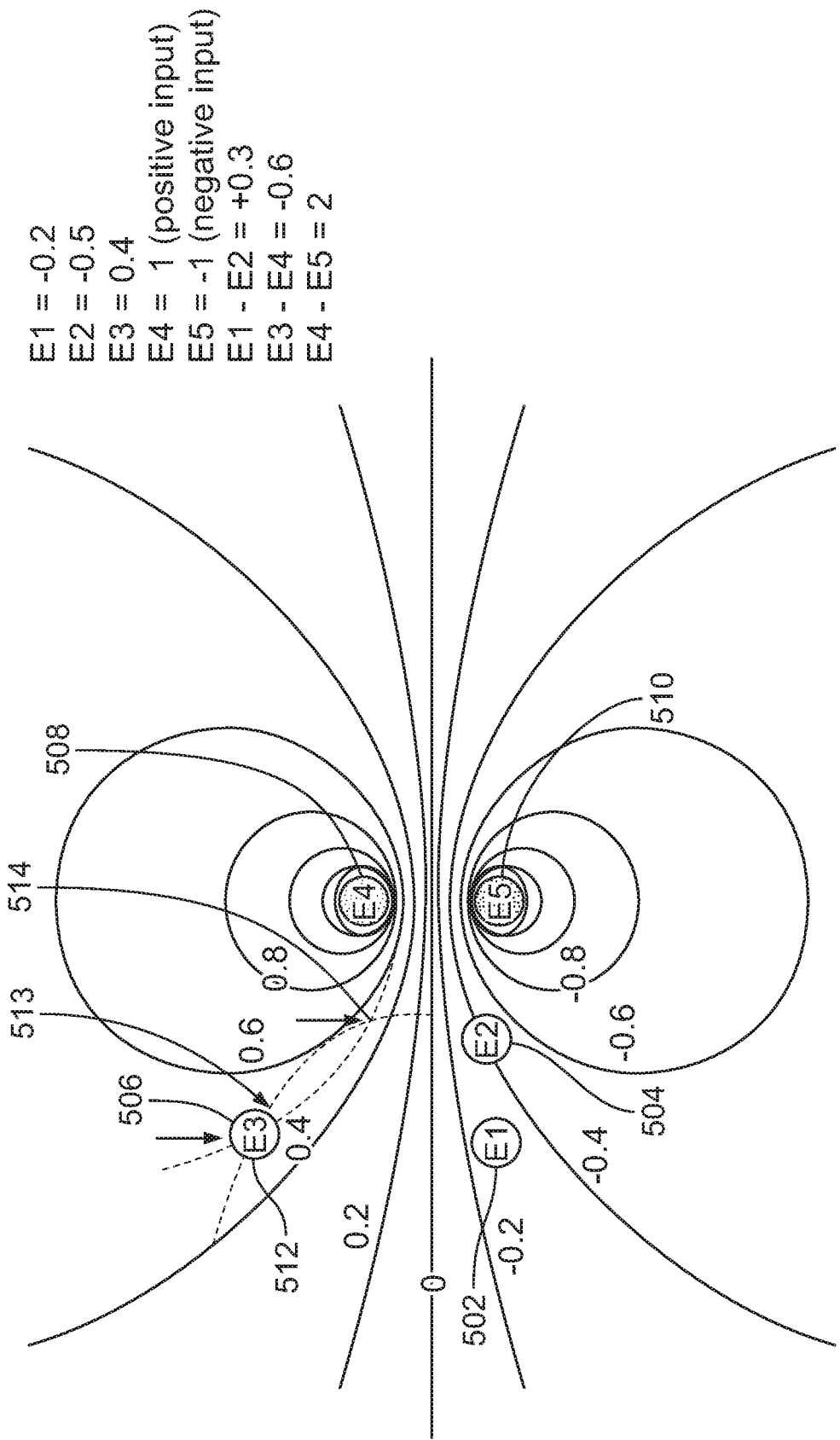
FIG. 5 illustrates the same exemplary set of electrodes in which a different field is generated using a different pair of injection electrodes.

Referring to FIG. 5, a different set of electrodes (relative to FIG. 4) are shown to be injected with signals, in accordance with another embodiment of the present specification. E4 508 is provided with a positive input voltage of 1V, and E5 510 is provided with a negative input voltage of −1V. In comparison to FIG. 4, which illustrates an identical positioning of all the electrodes, the expected output at each neighboring electrode that neighbors E4 508 and E5 510 changes. With reference to an indifferent electrode (e.g. FIG. 1B, electrode 118), E1 502 is now measured at −0.2V, E2 504 at −0.5V, and E3 506 at 0.4V. Further, the voltages measured across any combination of electrodes is different. For example, between E1 502 and E2 504 the difference is 0.3V, between E3 506 and E4 508 it is −0.6V, and between E4 508 and E5 510 it is 2V. Referring to the figure, E3 506 may be expected to be positioned at location 512 or at location 514, or anywhere else along the dotted lines 513 seen in FIG. 5. However, its actual location is further constrained when voltage measurement results from FIG. 4 and FIG. 5 are compared. In embodiments, as further different electrode combinations are used to inject signals, an estimate of an actual location of each electrode may be determined more accurately from the measured voltage values. In the stated example, if E3 406/506 is not positioned at its expected location, one or more values would be wrong. In some embodiments, an indifferent electrode is used for signal injection. In some embodiments, an indifferent reference is used for signal pickup/detection.

In various embodiments, if the electrodes are considered point sources, then the field around any injected signal is:

$$V_{signal} = V_{injected} * 1/r;$$

where: r is the distance between a first electrode used for injection and a second electrode used for pickup;
$V_{injected}$ is the voltage value of the injected signal at a first electrode; and
$V_{signal}$ is the voltage signal value that is measured at the second electrode that neighbors the first electrode.

In some embodiments, two closely spaced electrodes are used for positive and negative injection, then the field around the pair of electrodes is $$V_{signal} = V_{injected}(1/r_1 - 1/r_2);$$

where $r_1$ is the distance from the positive injector and the pickup electrode and $r_2$ is the distance from the negative injector and the pickup electrode.

Figure 6:
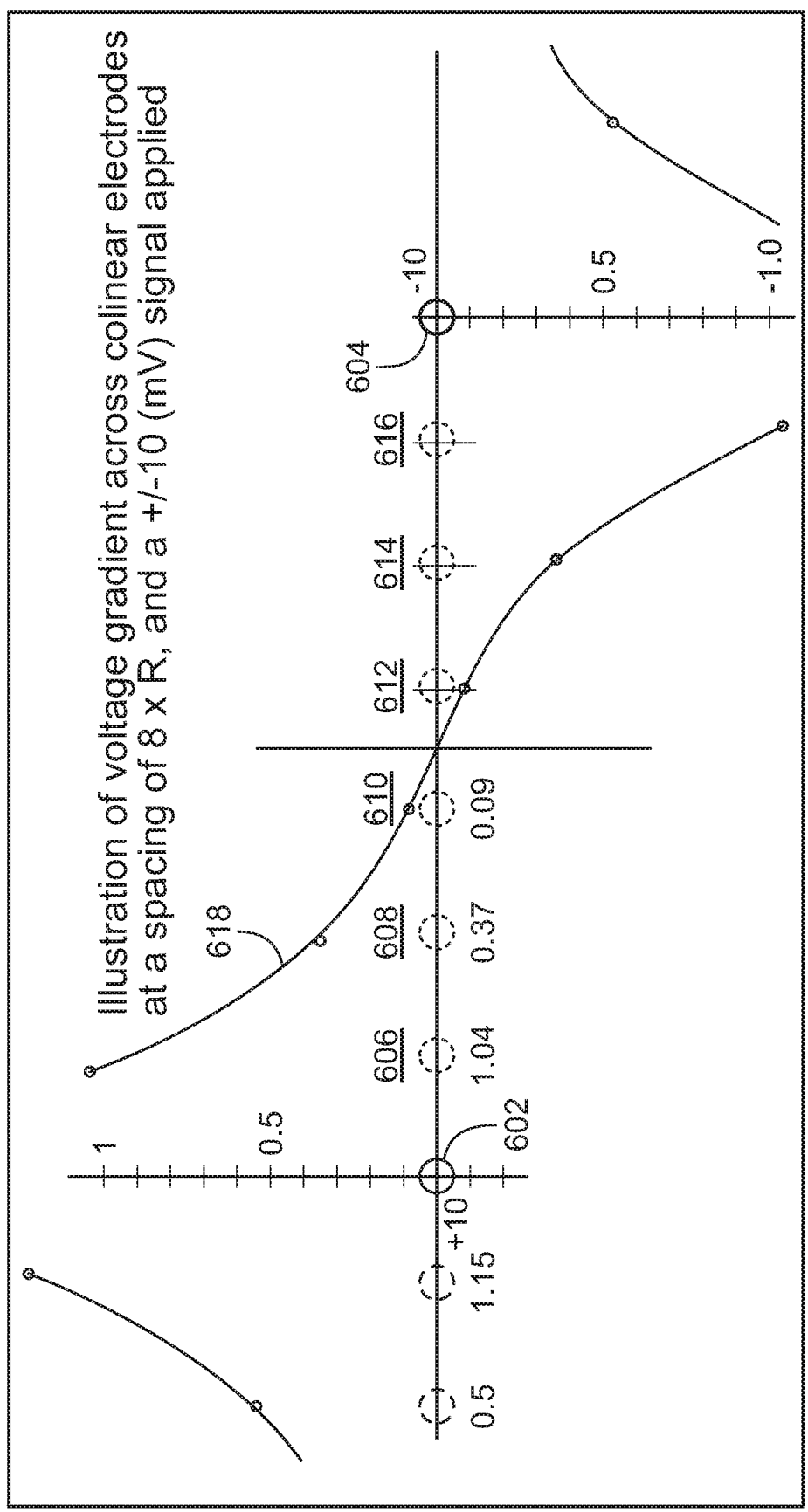
FIG. 6 illustrates a voltage gradient across collinear electrodes at a spacing of 8*R, and a +/−10 mV signal applied, in accordance with an embodiment of the present specification.

FIG. 6 illustrates a voltage gradient across collinear electrodes at a spacing of 8 contact radii and a +/−10 mV signal applied, in accordance with an embodiment of the present specification. Referring to the figure, a positive signal of +10 mV is injected to an electrode at position 602, and a negative signal of −10 mV is injected to another electrode at position 604. Between positions 602 and 604, other electrodes are collinearly and equidistantly placed at positions 606, 608, 610, 612, 614, and 616. A graph 618 of voltages measured at each intermittent position 606, 608, 610, 612, 614, and 616 shows that the value of the measured voltage reduces with an increase in a distance from the source electrodes at positions 602 and 604.

The brain, and especially the skull and skin, are not electrically homogeneous. Electrodes in the same type of tissue and electrodes that are closer together will have more predictable measurements than electrodes that are located in different tissue types (for example, brain versus scalp) or that are far apart. Therefore, measurements between electrodes, where all are positioned on the scalp, and measurements between electrodes positioned intracranially, where all are positioned on the brain are more reliable than measurements between electrodes where some are positioned on the scalp and some are positioned on the brain. In embodiments, the module computes the most reliable measurements, then computes the less reliable measurements with adjustments that estimate and account for the errors. The values measured for electrodes that are close together are given more weight than for electrodes that are far apart.

Grid electrodes are mechanically and electrically positioned on one side of a non-conductive carrier. Presence of the non-conductive carrier distorts the electric fields and results in an expected distortion, which may be estimated. The brain, facial and neck muscles and other sources of electrical artifact may also add uncertainty to the calculations. Module 125, based on the measurement, generates an estimate of the uncertainty for each measurement and has acceptance ranges for values based on the quality, or signal to noise ratio, of the measurements. Module 125 monitors each electrode and its neighbors, measuring the voltage at each, calculating the expected voltage, and determining the difference between the measured voltage and the expected voltage. Module 125 then weights the differences by expected voltage and combines the result into a single value termed the weighted average uncertainty.

In embodiments, if an electrode location fails to meet the expected value, then its actual location is estimated by solving an inverse problem. This method is described in context of co-pending United States Patent Publication No. 20180125421, U.S. Pat. Nos. 9,155,503, and 9,730,634, by the Applicants of the present specification, all of which are incorporated herein by reference. The inverse problem that is addressed relates to where an electrode would have to be located to generate or detect the signal that is measured.

For any one measurement, the distance from injector is proportional to $1/V_{measured}$, which describes a sphere around the injection point.

In some embodiments, the inverse problem may be solved for electrodes whose location is far outside their expected location. A number of such electrodes is expected to be a small number. In embodiments, the module knows when such an electrode cannot be clearly located and indicates the problem to the user.

A second injection point generates a second sphere, and the electrode would be constrained to the intersection of the two spheres which is a circle. A third injection point, located off axis to the first two, generates a third sphere whose intersection with the first two spheres would be one of two points. In embodiments, multiple injection points are used to constrain an electrode location to a single point, which can be described to a user, and which is different than the point that the electrode was expected to occupy.

Figures 7A, 7B:
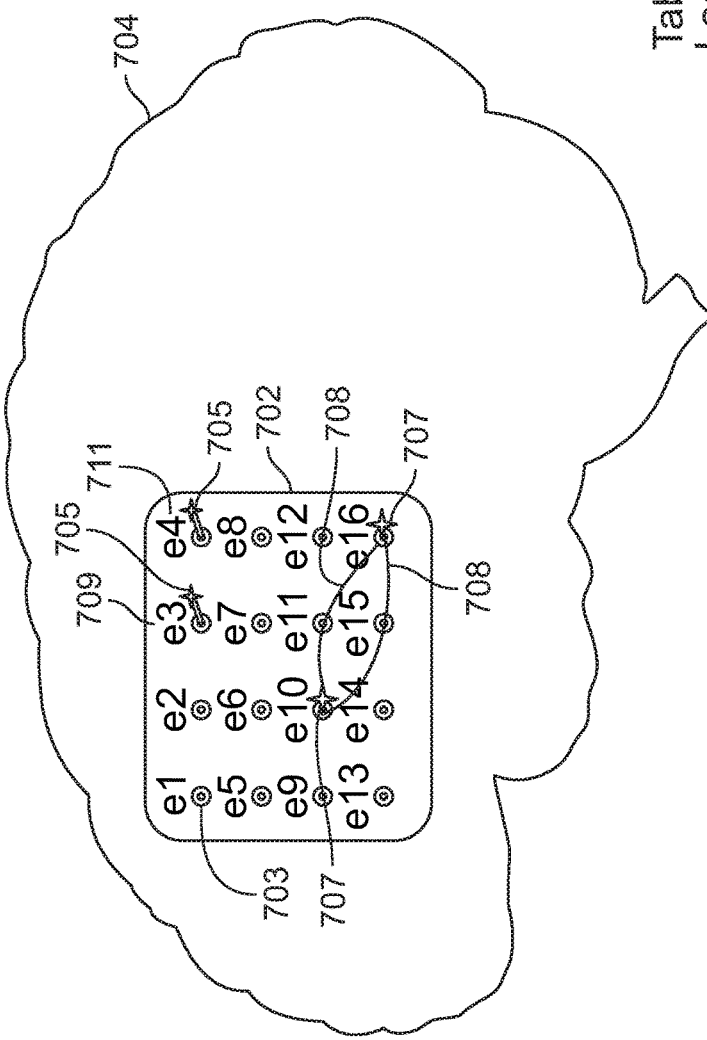
FIG. 7A illustrates an exemplary graphical display of electrode locations displayed to a user, in accordance with some embodiments of the present specification.
FIG. 7B illustrates an exemplary tabular display of electrode locations displayed to a user, in accordance with some embodiments of the present specification.

Errors due to noise, mathematical approximations and non-homogeneity generate a statistical location. The user can be shown graphically or in tabular format how closely the calculated location and the specified location are in agreement. FIG. 7A illustrates an exemplary graphical display of electrode locations displayed to a user, in accordance with some embodiments of the present specification. The display shows position of a grid of electrodes 702 on a layout 704 of a brain where electrodes 702 are placed. FIG. 7B illustrates an exemplary tabular display of electrode locations displayed to the user, in accordance with some embodiments of the present specification. If an error is detected by the module, a graphical presentation that highlights the difference between the expected and the measured locations may be shown to the user. The presentation may enable the user to visualize electrode movement, errors in electrode placement, errors in electrode connections, and electrodes that are not working properly. Referring to FIG. 7A, in an embodiment, an outline 703 or circle (gray in some embodiments) is used by the system to indicate specified electrode locations. Incorrect locations, identified as computed location errors, are indicated by visual indicators, such as stars 705, 707. In some embodiments, a blue star 705 indicates an alignment mechanism. For example, electrodes e3 709 and e4 711 have locations outside acceptable limits and are misaligned, as indicated by blue stars 705. Referring to FIG. 7B, the alignment errors 713 are listed in tabular display as 4 mm for e3 and 5 mm for e4. Referring again to FIG. 7A, electrodes e10 715 and e16 717 also have locations outside acceptable limits and are mislocated, as indicated by red stars 707. Referring to FIG. 7B, the location errors 719 are listed in tabular display as 23 mm for e10 and 24 mm for e16. In some embodiments, the red stars 707 are connected by lines 708 and together indicate a superimposing of an expected location, suggesting a potential misconnection. In other words, the red stars 707 and connecting lines 708 indicate electrodes e10 and e16 might have been swapped. In some embodiments, the input jacks, j42 721 for e16 and j36 723 for e10 are shown on the tabular display so the user may easily swap the inputs and check if that corrects the location error.

In operation, each electrode has a unique label, as described above in context of FIG. 2. Module 125 of FIG. 1C, and by extension the user, has the knowledge of the expected location of each of these electrodes. In some cases, such as misconnection, the user is informed which electrodes are misconnected. Labels of the electrodes are used to indicate the electrodes that are associate with errors. In embodiments, module 125 also knows which electrode jacks are assigned to which electrode positions, and the user can be informed which input jacks are misconnected.

If an actual error occurs in placement, connection, or electrode integrity, the error may be corrected and the algorithm is re-run to verify the new location and integrity.

In some embodiments, impedance of each electrode is measured. The impedance is used to weight the measurements performed previously. In some embodiments, impedance display and electrode location displays are integrated into the same graphical presentation.

In some embodiments, module 125 executes processes to organize the electrodes for best measurement. With a total of n number of electrodes positioned extracranial and intracranial, there are $n^2/2$ distance relations between the electrodes and n factorial (n!) injection and measurement opportunities. With more than 10-15 electrodes, the computation becomes computationally difficult to solve. In embodiments of the present specification, a selection algorithm is used to get meaningful results for a high number of electrodes. For example, the selection algorithm is used for 500 electrodes, which is a likely number. Therefore, factorial computational requirements are eliminated by module 125. The problem is reduced by finding a few close neighbors (typically adjacent contacts on the same group, grid, strip or depth electrode) of the electrodes, and measuring relative distances among neighbors, giving zero weight (and thus eliminating most of the calculations) to distant neighbors. This reduces the computational needs to (n*(number of neighbors)!). In some embodiments, the number of neighbors is chosen to be 4 or 5. Reducing the numbers improves the calculations and the computational efficiency, as most of the results from additional calculations would either be redundant (approximately the same and varying in the same manner with displacement) or very small and below the required signal to noise ratio.

In embodiments, module 125 also has metadata about the electrodes, grids and depth electrodes in particular, including that they are in fixed relations to each other. These relations can be computed and verified in smaller chunks, further reducing computational requirements.

Multiple errors may result in calculations that never converge. This may be a problem if the first few electrodes that are measured have the errors. In some embodiments, to alleviate the problem, both injection and pickup electrodes are removed from consideration in the first few passes if they cannot be verified. Once a number of electrodes are verified, the locations of the outliers is estimated using what are now good references.

Errors may also appear if there are metal implants in the skull of the patient, if the brain has large anatomic variations (including post resection), if there is a cranial defect, if there is an implanted stimulator, and if the instrument sees excessive artifact from movement, muscle tension, or other electrical equipment. In embodiments, module 125 reports such abnormalities to the user, and indicates the success and accuracy of electrode location. In situations where the physical electrode is distorted by the surgeon, then the distortion, missing electrodes, among other errors, are modified in the electrode model by module 125 to account for the changes.

To verify algorithmic robustness, the algorithm can solve the electrode location problem using inverse transforms. The results of this approach should match the location verification algorithm. Intra-cortical vs extra-cortical electrodes use the presence of the skull in estimating signals. During verification, the attenuation of the skull distorts the inverse estimates and the relations show an 'electrical' location which differs from the geometric location.

There are likely connection errors that can occur when plugging electrode leads into amplifier jacks, and these are specifically evaluated. A swap error is when two contiguous electrodes are interchanged. A rotation error is when an input is skipped or an electrode is skipped and a series of electrodes are connected one position away from their expected location. If the 'extra' electrode is then connected in the 'extra' input, the result is a rotation error.

Electrodes that are within an array or a linear strip can be reliably found to be in error due to swapping or rotation, either by single electrode or in combination or for any skipped inputs or electrodes.

In some embodiments, locations errors are determined by checking each 4×4 max array for errors, then proceeding to 4×8 or 8×8 arrays. In other embodiments, pigtail swapping is used to check for location errors.

For electrodes that are relatively far apart (for example, more than 3 cm apart), multiple injectors are used to compute these relatively large distances with more accuracy. Deciding if an electrode is or should be at a large distance can be determined from a specified location. Alternatively, the distance can first be estimated by using either one or multiple electrodes, then using an alternate set of electrodes to get a better estimate if needed. A preferred alternate set of electrodes would be collinear and orthogonal to the electrode whose position is being measured.

The positions of electrodes are relative. An observable electrode (on the scalp for example) in a known position is used, if available, to provide absolute positions for non-observable electrodes. The required number of observable electrodes, and their optimal positions, is part of module 125 that calculates a number of degrees of freedom and the accuracy and noise among various electrodes and contacts. The degrees of freedom, and its complement, the number of constraints to possible locations, changes with electrode count and number. For any pair of contacts (or an electrode with multiple pairs of this sort), there are 6 degrees of freedom, x, y, z, and yaw, pitch and roll. Each of these is continuously variable. It is assumed that the relative contact positions within an electrode are determined by electrode chosen and that the electrode contact geometry is fully constrained.

Actual electrode locations may be determined using a CT scan or x-ray and a co-registration process which allows using measured position instead of estimated or calculated position. The added precision may allow resolving real or apparent misconnections. In other instances, for example when an electrode is folded into a sulcus, the calculated locations may be significantly different than the measured locations even within one electrode.

Any single observable contact, or a contact that is known to be in a specific location and can be used as a reference, adds an absolute x,y,z location constraint, and four such contacts could fully constrain the system. Due to noise from electrical artifact, brain geometry and conductivity that does not match the model, among other errors, module 125 uses multiple estimates from multiple contacts in a manner that reduces the overall errors and generates the likelihood that a pair of electrodes are in the expected relation.

For multiple electrodes, the number of relations is $n^2$. In embodiments, a statistical likelihood that a pair of electrodes are in the expected relation is computed for each relation. In some embodiments, a Bayesian approach is used to estimate the probability of the resulting answer. In some embodiments, the likelihood is indicated as a value that is highly likely, somewhat likely, or not very likely. Each electrode may have a score related to all its relations, and the score for each electrode is shown on the display, preferably in a graphical and colored format. Electrodes that are misplaced, mis-rotated or misconnected may have aberrant scores to multiple other electrodes and may have lower likelihood of being correct. Electrodes that are correctly placed may only have an aberrant score relative to the misplaced electrodes, if any, and may have a higher likelihood of being correct. In embodiments, the statistics are generated for multiple contacts per electrode, and can have information on specific errors such as rotations or locations that are not as expected and by how much.

The electrode location verification module 125 is part of a workflow to verify proper location. Typically, a technician would run electrode location verification module 125 and use the output to fix, correct for, or explain reported errors. This process may be repeated after fixes or corrections.

Figure 8A:
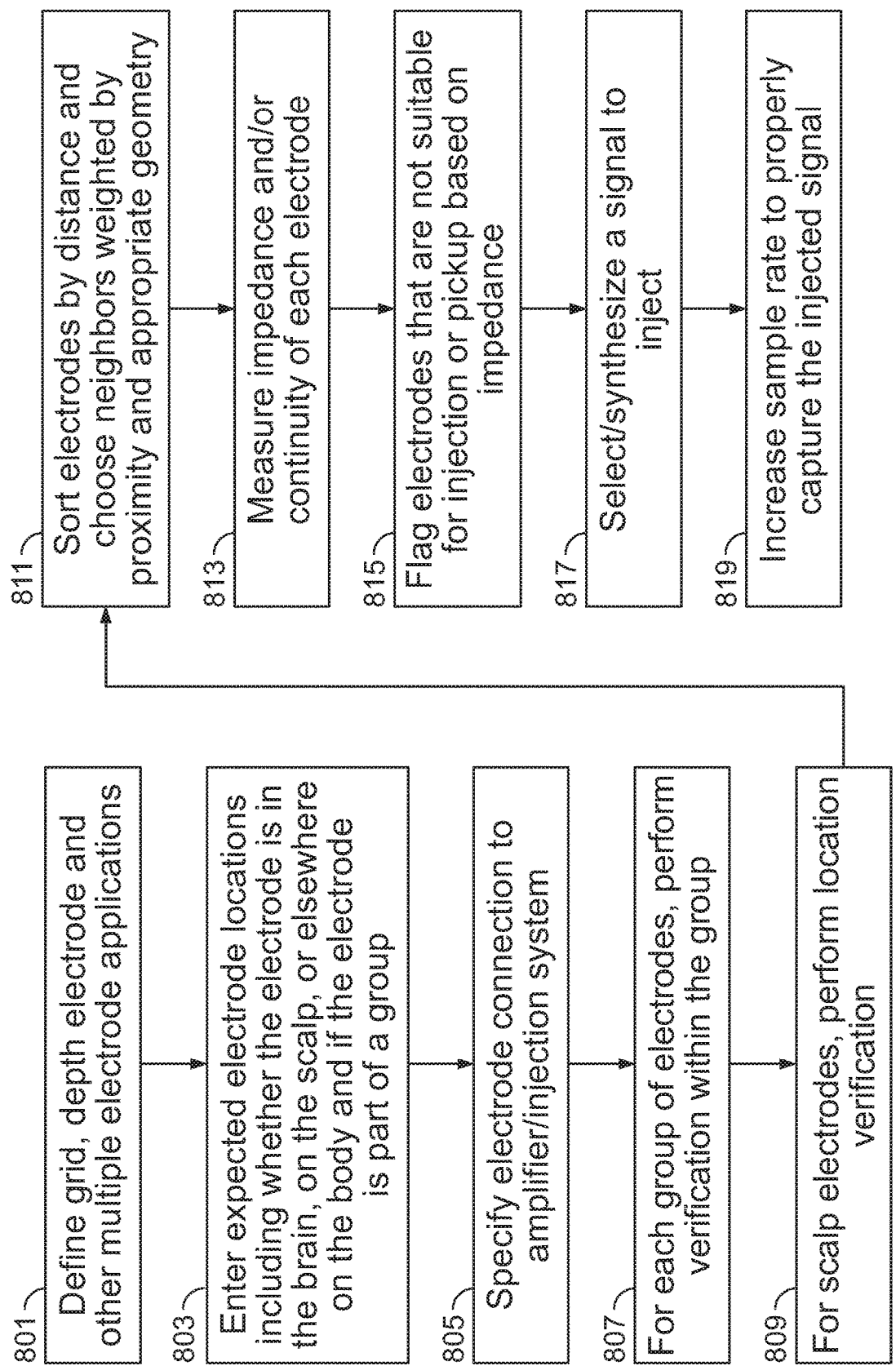
FIG. 8A is a flow chart illustrating an exemplary preparation process performed prior to and during an injection and measurement process used for location verification, in accordance with some embodiments of the present specification.

FIG. 8A is a flow chart illustrating an exemplary preparation process performed prior to and during an injection and measurement process used for location verification, in accordance with some embodiments of the present specification. At step 801, the grid, depth electrode and other multiple electrode applications are defined. At step 803, a user enters expected electrode locations, including whether the electrode is in the brain, on the scalp, or elsewhere on the body, and if the electrode is part of a group. This information may be automated to integrate surgical planning tools. The information will contain a minimum of the body site, or a 3D position that allows computing relative distances, orientation, and intracranial, extracranial or other location information. Names or references for all electrodes are available after this step. This information may be termed as the 'specified geometry', for purposes of this description. At step 805, electrode connections to an amplifier/injection system are specified. This may include individual connection, mass term connections, and identified connections. The channel assigned to each electrode is available after this step. At step 807, for each group of electrodes, location verification is performed within the group (for example, using the injection and measurement process described with reference to FIG. 8B). At step 809, for scalp electrodes (e.g. 10-20 EEG electrodes), location verification is performed. At step 811, electrodes are sorted by distance and neighbors are chosen weighted by proximity and appropriate geometry. Impedance and/or continuity of each electrode is measured at step 813. Electrodes that are not suitable for injection or pickup based on impedance are flagged at step 815. At step

817, the user selects/synthesizes a signal to inject. At step 819, the user increases a sample rate to properly capture the injected signal.

Figure 8B:
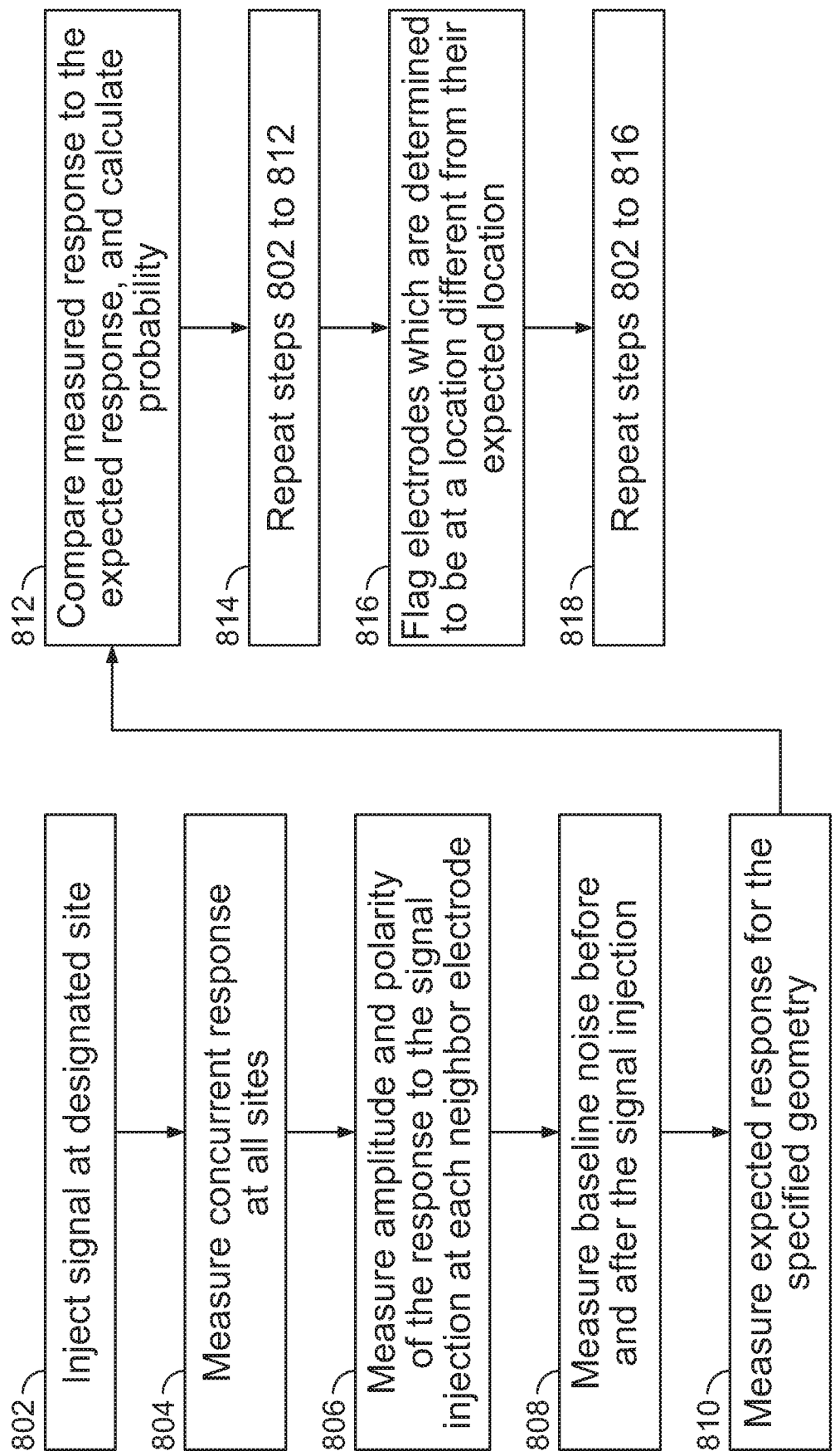
FIG. 8B is a flow chart illustrating an exemplary process executed by electrode location verification module, in accordance with some embodiments of the present specification.

FIG. 8B is a flow chart illustrating an exemplary process executed by an electrode location verification module, in accordance with some embodiments of the present specification. At 802, a signal is injected at a designated site. The injected signal, or input voltage, is provided to a pair of electrodes. One electrode in the pair is provided a positive input and the other a negative input of the same value. For purposes of this description, these electrodes may be referred to as the source electrodes. In embodiments, positive and negative are relative terms related to the measured signals. The injected signal(s) may be electrically positive, negative, biphasic, sinusoidal, complex or have arbitrary wave shape. At 804, the concurrent response at all sites is measured. In some embodiments, a response at the site of electrodes that neighbor the source electrodes is measured. In embodiments, neighbors are those electrodes that are closest to the source. This is because the signals are bigger (therefore better SNR) and the volume is more likely to be homogeneous in areas close together. In embodiments, the measurement includes a period of measurement before and after injecting input signal, for signal to noise calculations. At 806, the amplitude and polarity of the response to the signal injection is measured at each neighbor electrode. At 808, the baseline noise before and after the signal injection is measured.

At 810, the expected response for the specified geometry is measured. At 812, the measured response is compared to the expected response, and a probability that it is correct is computed. At 814, steps 802 to 812 are repeated using different set of injection electrodes that have geometric relations that cover x, y and z axis calculations. At 816, an electrode that is determined to be at a location different from its expected location is flagged. At 818, steps 802 to 816 are repeated for different combinations of source electrodes. While at 814, measurements are made on contacts whose positions are constrained by their presence on a grid, strip or depth electrode and, at 818, the relation of contacts on different electrodes is computed.

Figure 8C:
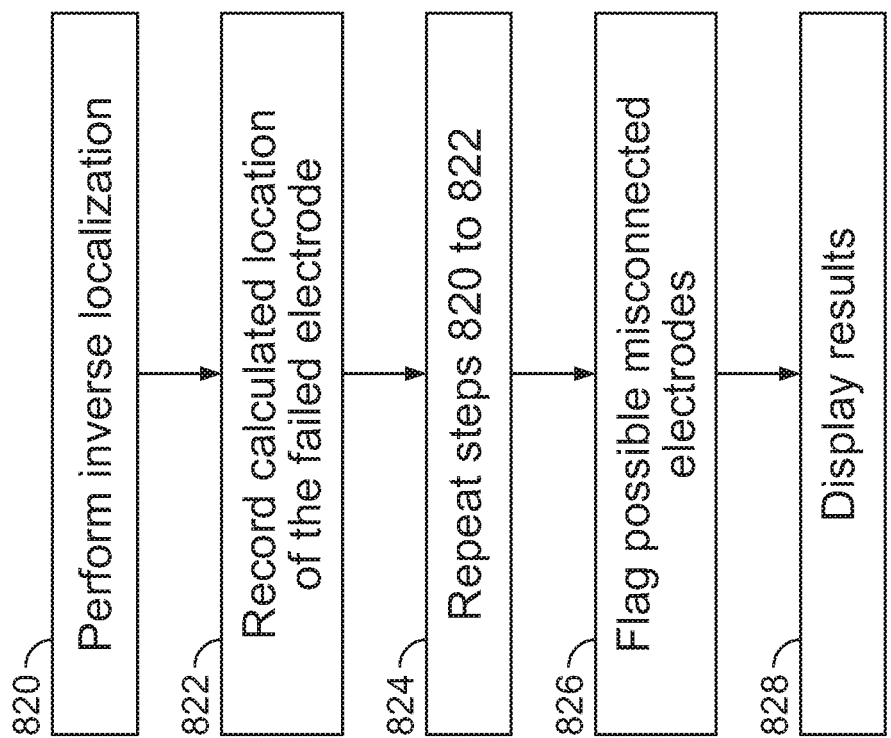
FIG. 8C is a flow chart illustrating an exemplary clean-up process performed after receiving location information from an injection and measurement process, in accordance with some embodiments of the present specification.

FIG. 8C is a flow chart illustrating an exemplary clean-up process performed after receiving location information from an injection and measurement process, in accordance with some embodiments of the present specification. The process described with reference to FIG. 8C may be performed after obtaining location results following the process of FIG. 8B. At 820, inverse localization is performed for electrodes (failed electrodes) that were identified to be at locations different from their expected locations, using electrodes known to be at their expected locations as injectors. Alternatively, the incorrect location identified for the failed electrodes is used to inject input signal and measure all likely neighbors. At 822, a calculated location of the failed electrode is recorded. At 824, steps 820 to 822 are repeated for each failed electrode. At 826, an electrode is flagged as a possible misconnect if it is determined to be at the expected location of another electrode. At 828, a graphical and/or tabular set of results is displayed to the user in accordance with the user's preferences. In some embodiments, the module generates a GUI (Graphical User Interface) to display one or more two and/or three-dimensional topographical maps or views of the patient's scalp such that the plurality of electrodes and their relative positioning on the scalp are correspondingly identified and marked or displayed on the maps.

Embodiments of the steps illustrated in the flow charts of FIGS. 8A-8C may be described by the various aspects of the specification described above in context of FIGS. 1A to 7.

Figure 9:
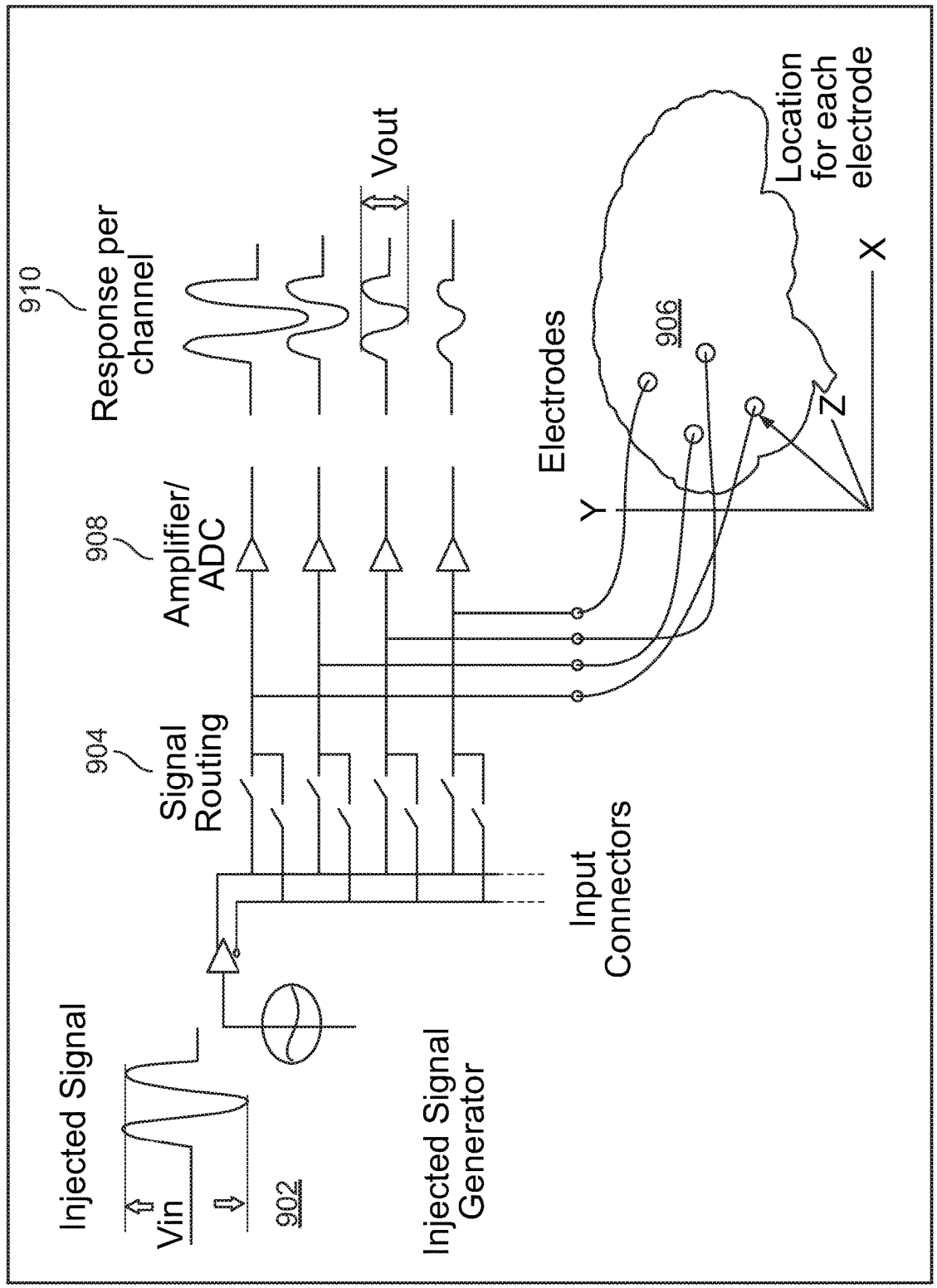
FIG. 9 illustrates a flow diagram of the steps performed by the various embodiments of the present specification in an exemplary system environment.

FIG. 9 illustrates a flow diagram of the steps performed by the various embodiments of the present specification in an exemplary system environment. In embodiments, a signal 902 is injected through a signal routing device 904 to electrodes 906. The injected signals and the measured signals are identified and routed through an amplifier 908 as response 910 for each channel.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A method for verifiying one or more locations of electrodes in a neuromonitoring system, the method comprising:

injecting a known signal, wherein the signal comprises a normal polarity and a reverse polarity that are respectively input to a first electrode and a second electrode, wherein the first electrode and the second electrode are surrounded by a plurality of neighboring electrodes, and wherein the injecting the signal generates an electric field around the first electrode, the second electrode, and the plurality of neighboring electrodes;

measuring concurrent responses to the electric field at the plurality of neighboring electrodes, wherein the measuring comprises measuring at least one amplitude, at least one polarity, and at least one waveform of the responses;

measuring a baseline noise at the first electrode, the second electrode, and the plurality of neighboring electrodes, before the injecting of the signal and after the injecting of the signal;

determining expected responses to the signal, at the plurality of neighboring electrodes for an expected geometry of the first electrode, the second electrode, and the plurality of neighboring electrodes;

comparing the measured concurrent responses to the expected responses;

flagging one or more electrodes of the plurality of neighboring electrodes for which the comparing determines that the respective measured response is different from the respective expected response, wherein the flagging indicates an incorrect location of the one or more flagged electrodes; and displaying at least the one or more flagged electrodes on a display.

2. The method of claim 1 wherein the first electrode, the second electrode, and the plurality of neighboring electrodes form an electrode group, and wherein each of said electrodes in the group has at least one of a similar monitoring functionality or a similar deployment location.

3. The method of claim 1 wherein the first electrode and the second electrode are extracranial electrodes and wherein the plurality of neighboring electrodes are at least one of intracranial electrodes or extracranial electrodes.

4. The method of claim 1 wherein the first electrode, the second electrode, and the plurality of neighboring electrodes are intracranial electrodes.

5. The method of claim 4 wherein the first electrode, the second electrode, and the plurality of neighboring electrodes are at least one of a group of grid electrodes, strip electrodes, or depth electrodes.

6. The method of claim 1 wherein the first electrode, the second electrode, and the plurality of neighboring electrodes comprise both extracranial electrodes and intracranial electrodes.

7. The method of claim 1 further comprising determining whether the one or more flagged electrodes are misconnected.

8. The method of claim 7 further comprising displaying the one or more misconnected electrodes on the display.

9. The method of claim 1 wherein the displaying comprises displaying at least one of a graph or a table, and wherein displaying distinguishes the one or more flagged electrodes from the remaining electrodes of the first electrode, the second electrode, and the plurality of neighboring electrodes.

10. The method of claim 1 wherein the comparing comprises:
assigning each of the plurality of neighboring electrodes a weight based on their respective position relative to the first electrode and the second electrode; and
considering the assigned weights during the comparing.

11. The method of claim 1 further comprises:
repeating the method while injecting the signal to a different combinations of electrodes from the group of the first electrode, the second electrode, and the plurality of neighboring electrodes;
evaluating the one or more flagged electrodes identified from each repetition, wherein the evaluating comprises performing a statistical evaluation; and
verifying locations of the first electrode, the second electrode, and the plurality of neighboring electrodes based on the evaluating.

12. A system for neuromonitoring comprising:
a first electrode;
a second electrode;
a plurality of neighboring electrodes, wherein the plurality of neighboring electrodes are configured to be located on a same side, front, or back of a patient's head, scalp, or brain as the first electrode and the second electrode and wherein the first electrode and the second electrode are surrounded by the plurality of neighboring electrodes;
a signal generator adapted to generate electrical signals and configured to inject the electrical signals into the first electrode and the second electrode, wherein the injecting generates an electric field around the first electrode, the second electrode, and the plurality of neighboring electrodes;
an amplifier connected to each of the first electrode, the second electrode, and the plurality of neighboring electrodes, wherein the amplifier is configured to receive responses to the electrical signals generated by the signal generator, convert the responses from an analog format to a digital format, and transmit the responses;
a control unit configured to:
receive the responses transmitted by the amplifier;
measure the responses to the electrical signals generated by the signal generator at the plurality of neighboring electrodes;
measure a baseline noise at the first electrode, the second electrode, and the plurality of neighboring electrodes, before the injecting of the signals and after the injecting of the signals;
determine expected responses to the electrical signals, at the plurality of neighboring electrodes for an expected geometry of the first electrode, the second electrode, and the plurality of neighboring electrodes;
compare the measured responses to the expected responses;
flag one or more electrodes of the plurality of neighboring electrodes for which the comparing determines that the respective measured response is different from the respective expected response, wherein the flagging indicates an incorrect location of the one or more flagged electrodes;
repeat the method while the electrical signals are injected to different combinations of electrodes from the group of the first electrode, the second electrode, and the plurality of neighboring electrodes;
evaluate the one or more flagged electrodes identified from each repetition, wherein the evaluating comprises performing a statistical evaluation; and
verify the locations of the first electrode, the second electrode, and the plurality of neighboring electrodes, based on the evaluating; and
a display for displaying at least the one or more flagged electrodes.

13. The system of claim 12 wherein the first electrode, the second electrode, and the plurality of neighboring electrodes form an electrode group, and wherein each of said electrodes in the electrode group has at least one of a similar monitoring functionality or a similar deployment location.

14. The system of claim 12 wherein the first electrode and the second electrode are extracranial electrodes and wherein the plurality of neighboring electrodes are at least one of intracranial electrodes or extracranial electrodes.

15. The system of claim 12 wherein the first electrode, the second electrode, and the plurality of neighboring electrodes are intracranial electrodes.

16. The system of claim 15 wherein the first electrode, the second electrode, and the plurality of neighboring electrodes are at least one of a group of grid electrodes, strip electrodes, or depth electrodes.

17. The system of claim 12 wherein the first electrode, the second electrode, and the plurality of neighboring electrodes comprise both extracranial electrodes and intracranial electrodes.

18. The system of claim 12 wherein said control unit is further configured to determine whether the one or more flagged electrodes are misconnected.

19. The system of claim 18 wherein the display is configured to display the one or more misconnected electrodes.

20. The system of claim 12 wherein the display is further configured to display at least one of a graph or a table, and wherein the displaying distinguishes the one or more flagged electrodes from the remaining of the first electrode, the second electrode, and the plurality of neighboring electrodes.

* * * * *